(12) United States Patent
Nakamura et al.

(10) Patent No.: US 8,739,781 B2
(45) Date of Patent: Jun. 3, 2014

(54) POWDER MEDICINE ADMINISTERING APPARATUS

(75) Inventors: Shigemi Nakamura, Isesaki (JP); Hisatomo Ohki, Isesaki (JP); Kazunori Ishizeki, Seta-gun (JP); Akira Yanagawa, Yokohama (JP)

(73) Assignees: Hitachi, Ltd., Tokyo (JP); Dott Limited Company, Yokohama-shi (JP)

( * ) Notice: Subject to any disclaimer, the term of this patent is extended or adjusted under 35 U.S.C. 154(b) by 968 days.

(21) Appl. No.: 12/267,180

(22) Filed: Nov. 7, 2008

(65) Prior Publication Data
US 2009/0120436 A1     May 14, 2009

(30) Foreign Application Priority Data

Nov. 9, 2007  (JP) ................................. 2007-291933
Sep. 5, 2008  (JP) ................................. 2008-228999

(51) Int. Cl.
*A61M 15/00*     (2006.01)
*B65D 83/06*     (2006.01)

(52) U.S. Cl.
USPC ................................. 128/203.15; 128/203.19

(58) Field of Classification Search
USPC ............. 128/203.12, 203.15, 203.21, 203.23, 128/200.24, 203.19
See application file for complete search history.

(56) References Cited

U.S. PATENT DOCUMENTS

| 4,046,146 | A | * | 9/1977 | Rosskamp et al. | ....... 128/203.15 |
| 5,033,463 | A | * | 7/1991 | Cocozza | ................. 128/203.21 |
| 5,394,868 | A | * | 3/1995 | Ambrosio et al. | ....... 128/203.15 |
| 5,702,362 | A | * | 12/1997 | Herold et al. | ................. 604/58 |
| 6,321,747 | B1 | * | 11/2001 | Dmitrovic et al. | ....... 128/203.15 |
| 6,332,461 | B1 | * | 12/2001 | Hyppola | ................. 128/203.15 |
| 2003/0116157 | A1 | * | 6/2003 | Braithwaite et al. | ..... 128/203.15 |
| 2004/0035420 | A1 | * | 2/2004 | Davies et al. | ............ 128/203.15 |

FOREIGN PATENT DOCUMENTS

| EP | 0 387 222 A1 | 9/1990 |
| EP | 0 451 745 A1 | 10/1991 |
| JP | 2003-175103 A | 6/2003 |
| WO | WO 96/08284 A2 | 3/1996 |

OTHER PUBLICATIONS

Partial European Search Report dated Feb. 17, 2009 (Ten (10) pages).

* cited by examiner

*Primary Examiner* — Jackie T Ho
*Assistant Examiner* — Peter S Vasat
(74) *Attorney, Agent, or Firm* — Crowell & Moring LLP

(57) ABSTRACT

A powder medicine administering apparatus includes: an upper body including a lower surface, and a medicine storage chamber having an upper opening portion opened on the lower surface; a lower body including an upper surface, and a medicine receiving chamber which has a lower opening portion, and which is recessed in a downward direction from the lower opening portion. The lower body is relatively slid with respect to the upper body so that the lower surface of the upper body is slidably moved on the upper surface of the lower body to be switched between a connection state and a non-connection state. The medicine receiving chamber is arranged to be moved in a one section from the standby position to the discharge position so that entire of the lower opening portion of the medicine receiving chamber is within the upper opening portion of the upper body.

16 Claims, 15 Drawing Sheets

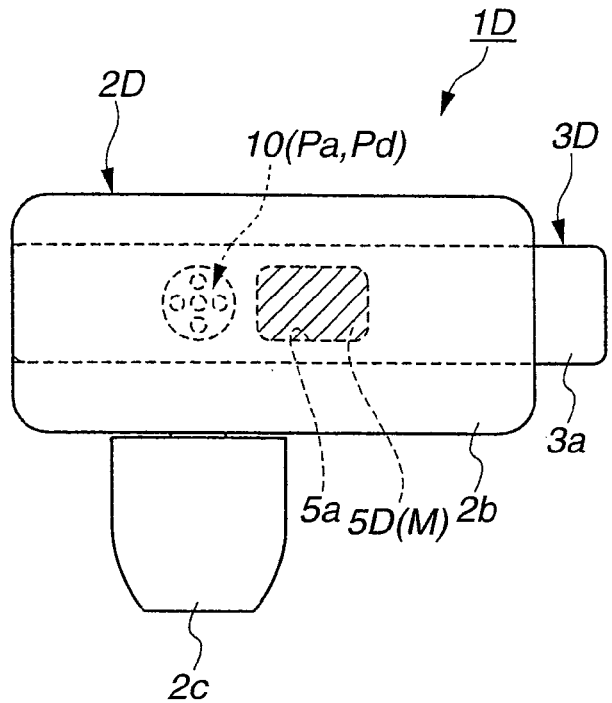
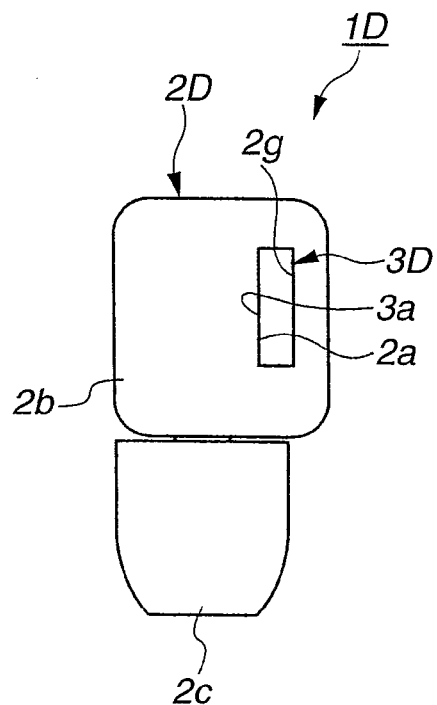
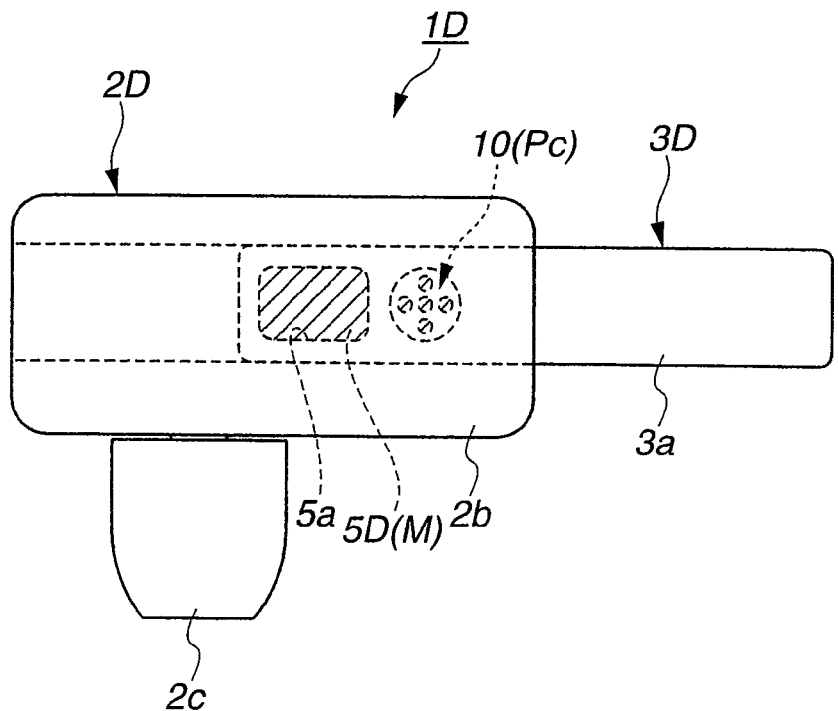

POWDER MEDICINE ADMINISTERING APPARATUS

BACKGROUND OF THE INVENTION

The present invention relates to a powder medicine administering apparatus.

Japanese Patent Application Publication No. 2003-175103 shows a powder medicine administering apparatus arranged to level a powder medicine supplied from a medicine storage chamber to a medicine receiving chamber, and to discharge a measured (constant) amount of the powder medicine with the air.

SUMMARY OF THE INVENTION

However, the above-described powder medicine administering apparatus has insufficient ability to level the powder medicine. In this powder medicine administering apparatus, the powder medicine may be insufficiently filled to the medicine receiving chamber.

It is an object of the present invention to provide a powder medicine administering apparatus arranged to improve a filling rate of a powder medicine to a medicine receiving chamber.

According to one aspect of the present invention, a powder medicine administering apparatus comprises: an upper body including a lower surface, and a medicine storage chamber having an upper opening portion opened on the lower surface, and storing a powder medicine; a lower body including an upper surface, and a medicine receiving chamber which has a lower opening portion, and which is recessed in a downward direction from the lower opening portion, the lower body being relatively slid with respect to the upper body so that the lower surface of the upper body is slidably moved on the upper surface of the lower body to be switched between a connection state in which the upper opening portion of the upper body is connected with the medicine receiving chamber of the lower body, and a non-connection state in which the upper opening portion of the upper body is not connected with the medicine receiving chamber of the lower body, the medicine storage chamber of the upper body being arranged to supply the powder medicine through the upper opening portion of the upper body to the medicine receiving chamber of the lower body in the connection state, the upper body being arranged to level the powder medicine supplied to the medicine receiving chamber by the relative slide movement of the upper body and the lower body, the medicine receiving chamber being moved from a standby position to a discharge position in which the medicine receiving chamber is connected with an air passage to discharge the powder medicine with an air, the medicine receiving chamber being arranged to be moved in a one section from the standby position to the discharge position so that entire of the lower opening portion of the medicine receiving chamber is within the upper opening portion of the upper body.

According to another aspect of the invention, a powder medicine administering apparatus comprises: an upper body including a lower surface, and a medicine storage chamber having an upper opening portion opened on the lower surface, and storing a powder medicine; a lower body including an upper surface, and a medicine receiving chamber which has a lower opening portion, and which is recessed in a downward direction from the lower opening portion, the lower body being relatively slid with respect to the upper body so that the lower surface of the upper body is slidably moved on the upper surface of the lower body to be switched between a connection state in which the upper opening portion of the upper body is connected with the medicine receiving chamber of the lower body, and a non-connection state in which the upper opening portion of the upper body is not connected with the medicine receiving chamber of the lower body, the medicine storage chamber of the upper body being arranged to supply the powder medicine through the upper opening portion of the upper body to the medicine receiving chamber of the lower body in the connection state, the upper body being arranged to level the powder medicine supplied to the medicine receiving chamber by the relative slide movement of the upper body and the lower body, the medicine receiving chamber being moved to a discharge position in which the medicine receiving chamber is connected with an air passage to discharge the powder medicine with an air, the medicine receiving chamber being arranged to reach the discharge position after at least two strokes that the medicine receiving chamber is switched from the non-connection state through the connection state to the non-connection state by passing the medicine receiving chamber below the upper opening portion of the medicine storage chamber by the relative slide movement of the upper body and the lower body to supply and level the powder medicine.

According to still another aspect of the invention, a powder medicine administering method for a powder medicine administering apparatus including an upper body including a lower surface, and a medicine storage chamber having an upper opening portion opened on the lower surface, and storing a powder medicine; a lower body including an upper surface, and a medicine receiving chamber which has a lower opening portion, and which is recessed in a downward direction from the lower opening portion, the powder medicine administering method comprises: slidably sliding the lower body with respect to the upper body so that the lower surface of the upper body is slidably moved on the upper surface of the lower body to be switched between a connection state in which the upper opening portion of the upper body is connected with the medicine receiving chamber of the lower body, and a non-connection state in which the upper opening portion of the upper body is not connected with the medicine receiving chamber of the lower body; supplying the powder medicine from the medicine storage chamber of the upper body through the upper opening portion of the upper body to the medicine receiving chamber of the lower body in the connection state; leveling the powder medicine supplied to the medicine receiving chamber by the upper body the by the relative slide movement of the upper body and the lower body; moving the medicine receiving chamber from a standby position to a discharge position in which the medicine receiving chamber is connected with an air passage to discharge the powder medicine with an air; and moving the medicine receiving chamber in a one section from the standby position to the discharge position so that entire of the lower opening portion of the medicine receiving chamber is within the upper opening portion of the upper body.

BRIEF DESCRIPTION OF THE DRAWINGS

FIGS. 25A and 25B show a powder medicine administering apparatus according to a third embodiment of the present invention. FIG. 25A is a plan view showing the powder medicine administering apparatus when a medicine receiving chamber is on one side of a relative sliding direction with respect to a medicine storage chamber. FIG. 25B is a side view showing the powder medicine administering apparatus of FIG. 25A.

FIG. 26 is a plan view showing the powder medicine administering apparatus of FIG. 25A when the medicine receiving chamber is on the other side of the relative sliding direction with respect to the medicine storage chamber.

DETAILED DESCRIPTION OF THE INVENTION

Figure 1:
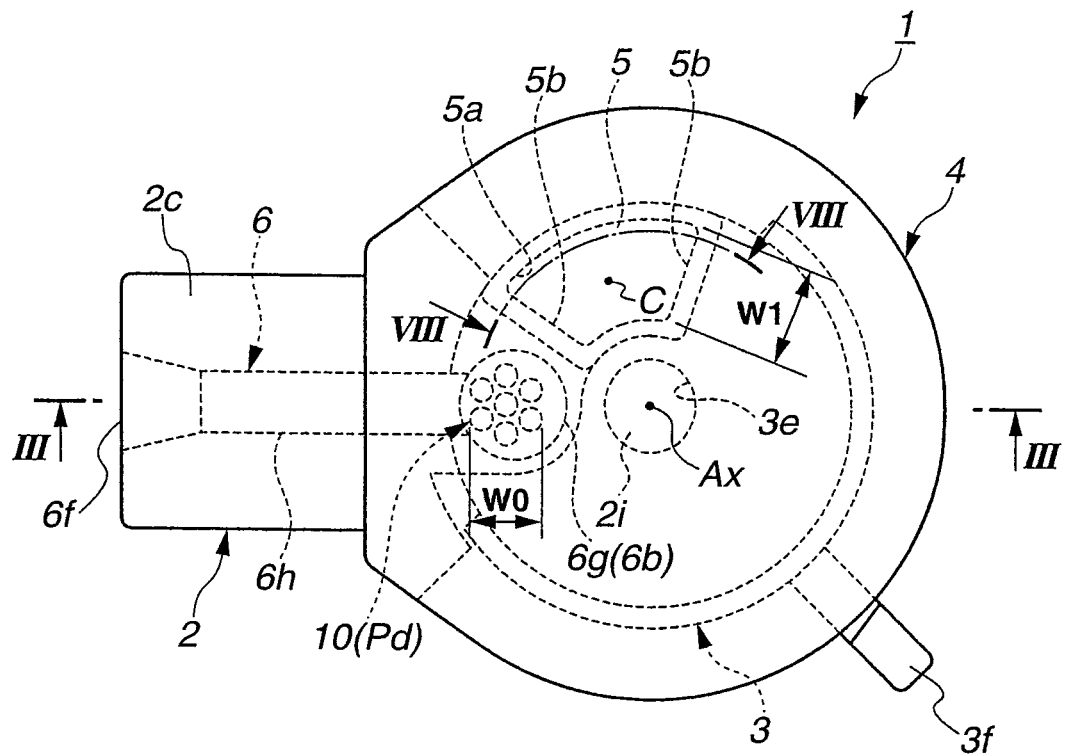
FIG. 1 is a plan view (top view) showing a powder medicine administering apparatus when a medicine receiving chamber is in a discharge position (wait or standby position), according to a first embodiment of the present invention.

Hereinafter, embodiments according to the present invention will be illustrated in detail. In the embodiments illustrated below, the invention is applied to a powder medicine administering apparatus of an oral type. The powder medicine administering apparatuses according to the embodiments are substantially identical to each other in most aspects as shown by the use of the same reference numerals.

Figure 2:
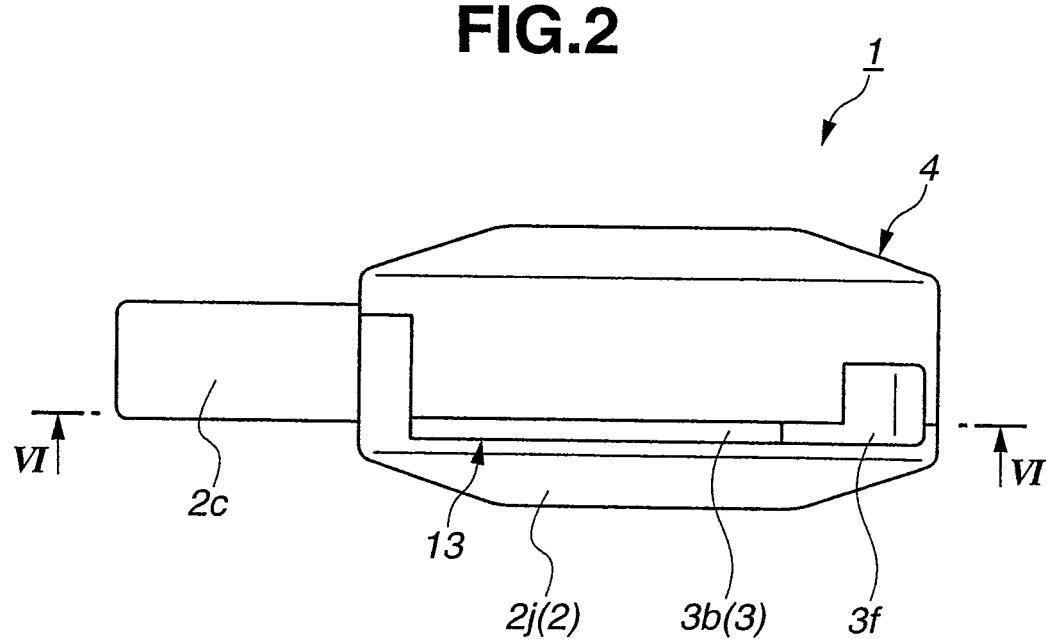
FIG. 2 is a side view showing the powder medicine administering apparatus of FIG. 1 when the powder medicine administering apparatus in a non-use state and the medicine receiving chamber is in the discharge position (wait position).
Figure 3:
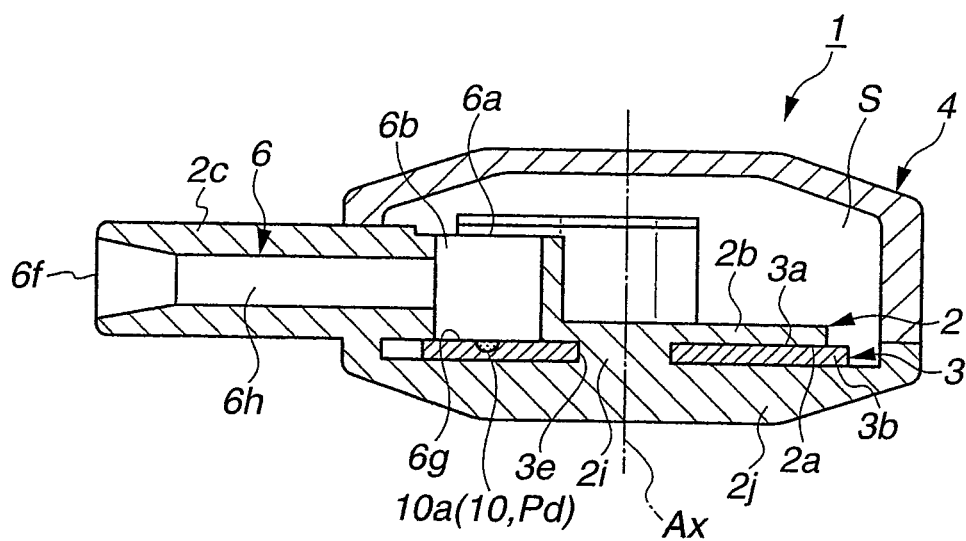
FIG. 3 is a sectional view taken along a section line III-III of FIG. 1.
Figure 4:
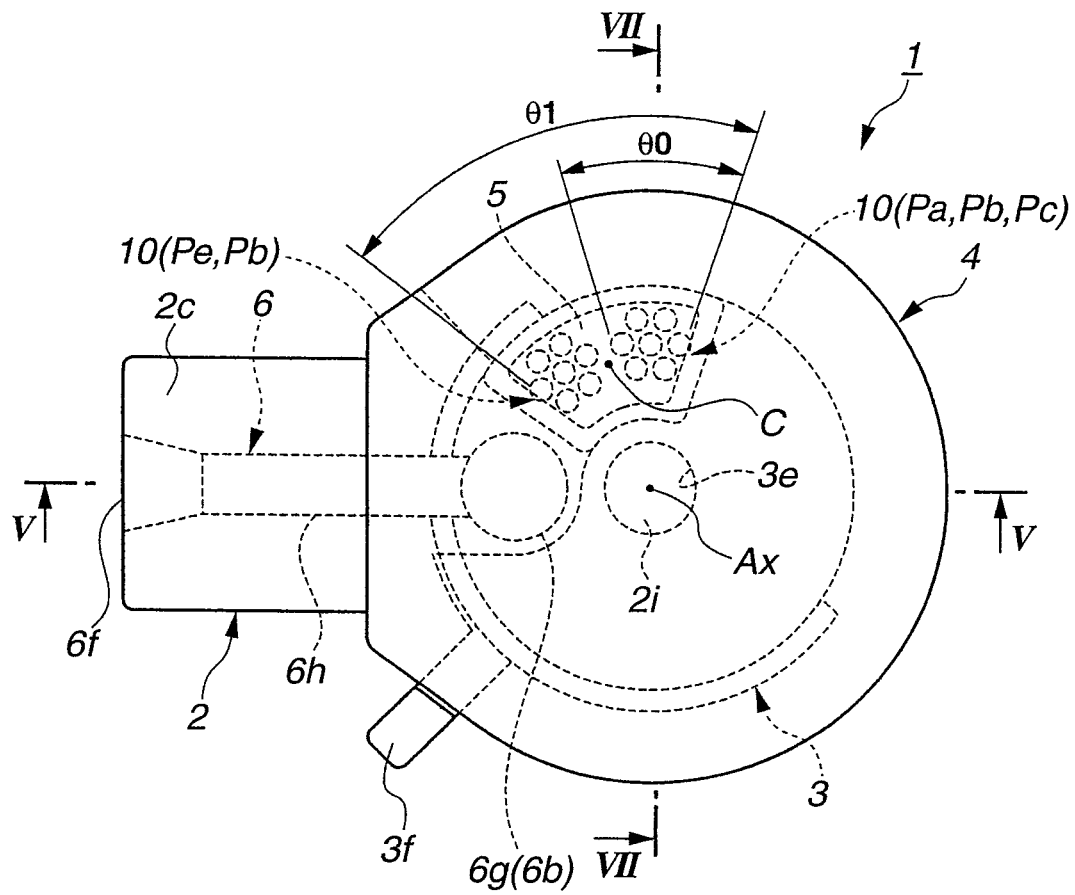
FIG. 4 is a plan view (top view) showing the powder medicine administering apparatus of FIG. 1 when the medicine receiving chamber is in a filling position.
Figure 5:
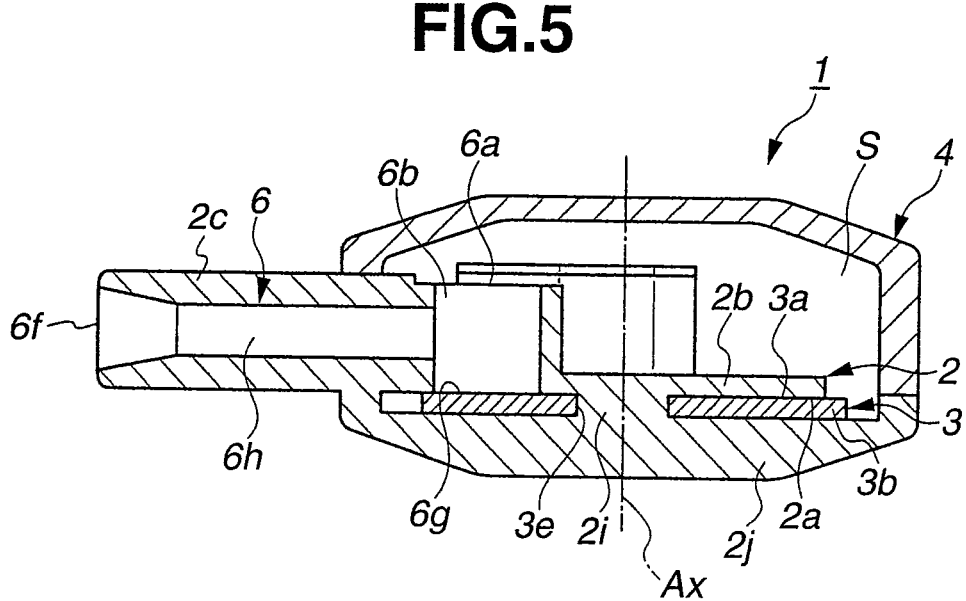
FIG. 5 is a sectional view taken along a section line V-V of FIG. 4.
Figure 6:
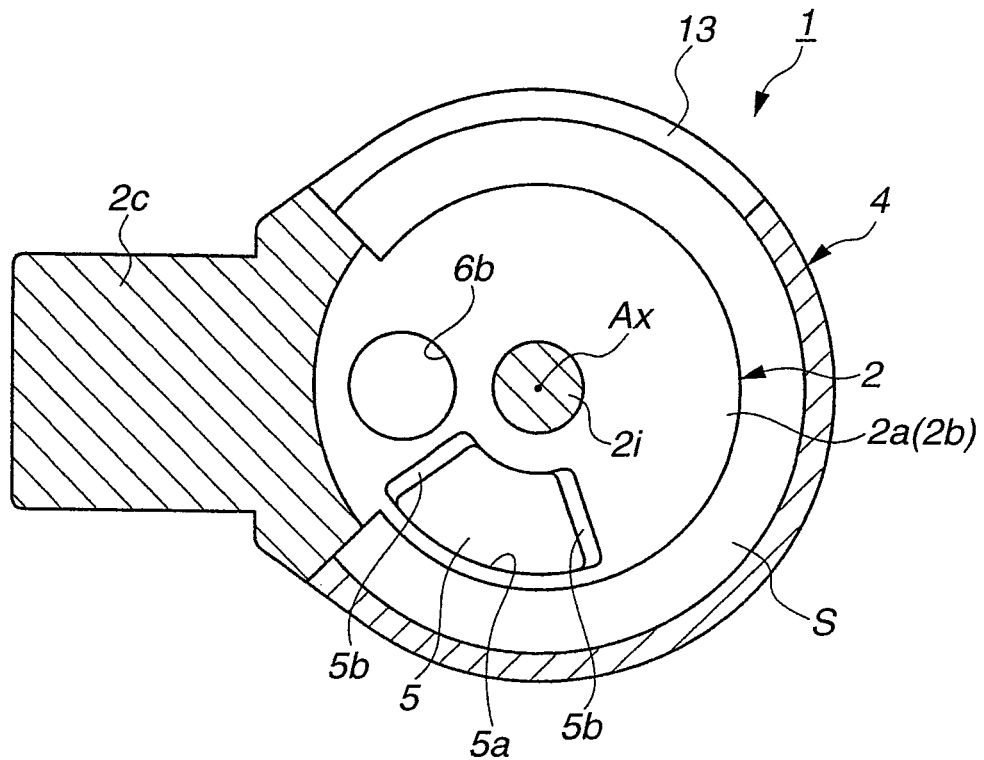
FIG. 6 is a sectional view taken along a section line VI-VI of FIG. 2.
Figure 7:
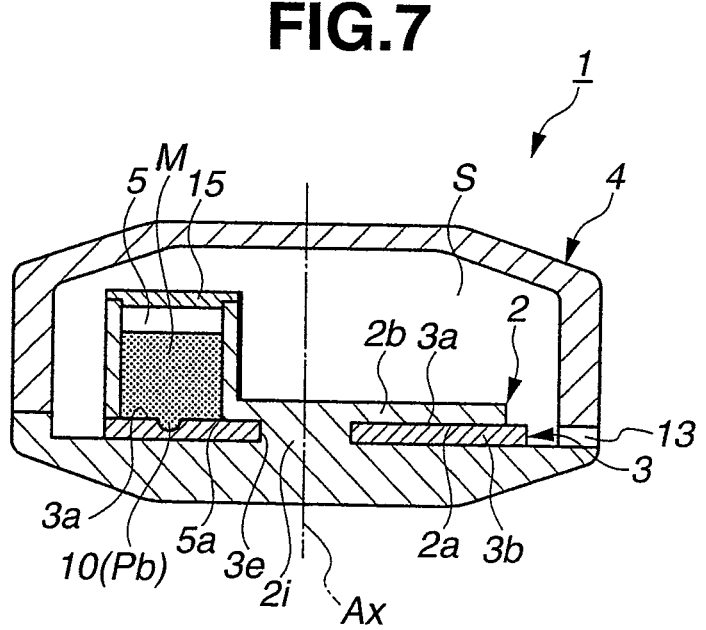
FIG. 7 is a sectional view taken along a section line VII-VII of FIG. 4.
Figure 8:
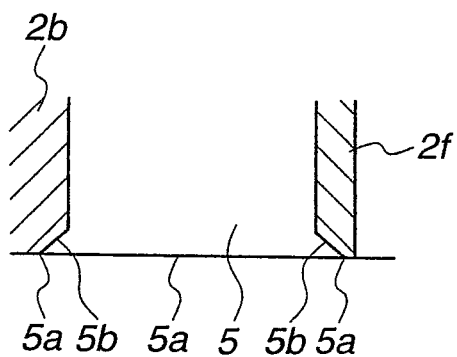
FIG. 8 is a sectional view taken along a sectional line VIII-VIII of FIG. 1.
Figure 9A:
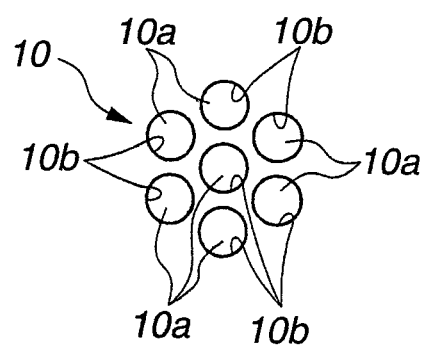
FIG. 9A is a plan view showing the medicine receiving chamber of the powder medicine administering apparatus of FIG. 1.
Figure 9B:
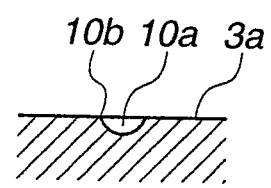
FIG. 9B is a partial sectional view showing the medicine receiving chamber of the powder medicine administering apparatus of FIG. 1.

FIGS. 1~7 show a powder medicine administering apparatus according to a first embodiment of the present invention. FIG. 1 is a plan view (top view) showing the powder medicine administering apparatus when a medicine receiving chamber is in a discharge position. FIG. 2 is a side view showing the powder medicine administering apparatus when the medicine receiving chamber is in the discharge position. FIG. 3 is a sectional view taken along a section line III-III of FIG. 1. FIG. 4 is a plan view (top view) showing the powder medicine administering apparatus when the medicine receiving chamber is in a filling position (wait or standby position). FIG. 5 is a sectional view taken along a section line V-V of FIG. 4. FIG. 6 is a sectional view taken along a section line VI-VI of FIG. 2. FIG. 7 is a sectional view taken along a section line VII-VII of FIG. 4. FIG. 8 is a sectional view taken along a sectional line VIII-VIII of FIG. 1. FIG. 9A is a plan view showing the medicine receiving chamber of the powder medicine administering apparatus of FIG. 1. FIG. 9B is a partial sectional view showing the medicine receiving chamber of the powder medicine administering apparatus of FIG. 1.

As shown in FIGS. 1~7, powder medicine administering apparatus 1 includes an upper body 2 and a lower body 3 which are arranged to be relatively slid with each other. Upper body 2 and lower body 3 include, respectively, disc portions 2*b* and 3*b* which are overlapped with each other in the upward and downward directions. Disc portion 2*b* of upper body 2 includes a substantially annular lower surface 2*a*. Disc portion 3*b* of lower body 3 includes a substantially annular upper surface 3*a* arranged to be slid on lower surface 2*a* of disc portion 2*b*. Upper body 2 includes a substantially cylindrical shaft portion 2*i* which is located at a substantially central portion of disc portion 2*b* of upper body 2, and which extends vertically from lower surface 2*a* in the downward direction. Lower body 3 includes a through hole 3*e* which is located at a substantially central portion of disc portion 3*b*, and which extends vertically from the upper surface 3*a* in the downward direction. Shaft portion 2*i* of upper body 2 is pivotally inserted into through hole 3*e* of lower body 3. That is, upper body 2 and lower body 3 are relatively pivoted (slid) about a central axis (pivot axis Ax) of shaft portion 2*i* and through hole 3*e*. Consequently, lower surface 2*a* of upper body 2 and upper surface 3*a* of lower body 3 are relatively slid with each other in a circumferential direction. Upper body 2 includes a bottom wall portion 2*j* located below lower body 3. Shaft portion 2*i* extends between disc portion 2*b* and bottom wall portion 2j. Disc portion 3b of lower body 3 is sandwiched between disc portion 2b and bottom wall portion 2j of upper body 2.

As shown in FIGS. 1~5, upper body 2 includes a tubular (cylindrical) portion 2c which is located on a side surface of disc portion 2b of upper body 2, and which extends radially outwards. As shown in FIGS. 1 and 3, tubular portion 2c includes an air passage 6 having a discharge opening 6f located at an end portion of tubular portion 2c. The air and the powder medicine (stirred flow of the air and the powder medicine) are discharged from discharge opening 6f.

As shown in FIGS. 1~5, there is provided a cover 4 which has a bottomed cylindrical shape opened in the downward direction, and which covers upper body 2 from the above. As shown in FIG. 2, there is formed a slit 13 between a lower end of cover 4 and an upper end of upper body 2. Lower body 3 includes a handle portion 3f protruding radially outwards from disc portion 3b of lower body 3 through slit 13 beyond cover 4 and upper body 2. By operating this handle portion 3f, lower body 3 can be relatively pivoted (slid) with respect to upper body 2. In this case, region (length) of slit 13 is arbitrarily set, and accordingly it is possible to set operation range of handle 3, that is, range of relative pivot movement (relative slide movement) of lower body 3 with respect to upper body 2. In this embodiment, slit 13 connects a space S within cover 4 and the outside, and accordingly the air can flow through air passage 6.

Air passage 6 is formed in upper body 2, as shown in FIG. 3. Air passage 6 includes an inlet opening 6a opened in an upper surface of upper body 2; a passage 6b extending from inlet opening 6a within upper body 2 in the upward and downward directions; and a passage 6h extending from a middle portion of passage 6b on the lower end's side, through the inside of tubular portion 2c to the discharge (outlet) opening 6f.

As shown in FIGS. 1 and 3, in the use state, an opening portion 6g which is located at a lower portion of passage 6b is overlapped (covered) with medicine receiving chamber 10 which is filled with powder medicine M, and medicine receiving chamber 10 is connected with (confronts) air passage 6. That is, in this state, medicine receiving chamber 10 is located at a discharge position Pd. In this use state, the user holds tubular portion 2c in the user's mouth, and sucks. The air flow is generated in air passage 6, the air and powder medicine M within medicine receiving chamber 10 are stirred in passages 6b and 6h. The mixed flow of the air and powder medicine M is absorbed from discharge opening 6f to the mouth of the user.

As shown in FIG. 7, a medicine storage chamber 5 stores powder medicine M. Medicine storage chamber 5 is a substantially sealed space surrounded by a through hole penetrating through disk portion 2b of upper body 2 in the upward and downward directions, and having a substantially sectorial section (cf. FIGS. 1, 4 and 6) which is concentric with pivot axis Ax, upper surface 3a of lower body 3 which closes the lower end of the through hole, and a cap 15 which closes the upper end of the through hole. The lower end of the through hole of medicine storage chamber 5 is an opening portion (upper opening portion) 5a. Powder medicine M within medicine storage chamber 5 is filled through this opening portion 5a to medicine receiving chamber 10 formed in upper surface 3a of lower body 3. The filling of powder medicine M to medicine receiving chamber 10 will be illustrated later.

As shown in FIG. 8, opening portion 5a of medicine storage chamber 5 includes inclined surfaces 5b which are located at both circumferential ends of opening portion 5a in the circumferential direction (relative sliding direction), whose edges are cut off (chamfered), and which are inclined so that an opening area of opening portion 5a increases toward the open direction (the upper surface 3a's side).

FIG. 9A is a plan view showing the medicine receiving chamber. FIG. 9B is a partially sectional view showing the medicine receiving chamber. As shown in FIG. 9, medicine receiving chamber 10 is a recessed portion formed in upper surface 3a of lower body 3. In this embodiment, medicine receiving chamber 10 includes a plurality of arranged small holes 10a each of which is in the shape of dimple. Each of small holes 10a includes an opening portion (lower opening portion) 10b having an area which is smaller than opening portion (upper opening portion) 5a of medicine storage chamber 5.

FIGS. 4 and 5 are views showing a state before the use, in which medicine receiving chamber 10 is in the standby position Pa. In this state, opening portion 5a of medicine storage chamber 5 covers medicine receiving chamber 10 as shown in FIG. 7, powder medicine M within medicine storage chamber 5 is filled by the gravity through opening portion 5a to medicine receiving chamber 10. In this case, medicine receiving chamber 10 is in the filling position Pb, and opening portion 5a of medicine storage chamber 5 and medicine receiving chamber 10 are in the connection state. In a state shown in FIGS. 4 and 7, all of the plurality of small holes 10a of medicine receiving chamber 10 are within opening portion 5a of medicine storage chamber 5.

The user moves handle portion 3f from the state shown in FIGS. 4 and 5 so that lower body 4 is relatively pivoted with respect to upper body 2 in the counterclockwise direction of FIG. 4, and consequently the powder medicine administering apparatus is brought to the state shown in FIGS. 1 and 3. In this state, medicine receiving chamber 10 filled with powder medicine M is connected through opening portion 6g to air passage 6. That is, medicine receiving chamber 10 is in discharge position Pd. Inlet opening 6a and discharge opening 6f of air passage 6 are connected with the outside air, so that the air can flow. Accordingly, when the air flow is in generated in air passage 6 by the suction of the user, powder medicine M filled within medicine receiving chamber 10 is effectively raised up by the air entered from passage 6b, and stirred with the air. Consequently, powder medicine M is effectively inserted into the mouth of the user.

The user moves handle portion 3f after the use so that lower body 3 is relatively pivoted with respect to upper body 2 in the clockwise direction of FIG. 1, and consequently the powder medicine administrating apparatus is brought to the state shown in FIGS. 4 and 5.

In the case in which the powder medicine administrating apparatus is brought from the state of FIGS. 4 and 5 through the state of FIGS. 1 and 3 to the state of FIGS. 4 and 5 as described above, the position relationship between opening portion 5a of medicine storage chamber 5 and medicine receiving chamber 10 is varied, medicine receiving chamber 10 moves back and forth (reciprocates) in the relative sliding direction (in the circumferential direction in FIGS. 1 and 4) below opening portion 5a of medicine storage chamber 5. While medicine receiving chamber 10 is overlapped with opening portion 5a, powder medicine M is filled through opening portion 5a to medicine receiving chamber 10. After medicine receiving chamber 10 is not overlapped with opening portion 5a, powder medicine M of medicine receiving chamber 10 is leveled by lower surface 2a of upper body 2. The above transition is one stroke that opening portion 5a and medicine receiving chamber 10 are brought from the non-connection state through the connection state to the non-connection state to introduce powder medicine M into medicine receiving chamber 10, and to level powder medicine M.

In this example, there is a one section (leg) in which medicine receiving chamber 10 is moved so that entire opening portions (lower opening portions) 10b of medicine receiving chamber 10 are within opening portion (upper opening portion) 5a of medicine storage chamber 5 when medicine receiving chamber 10 is moved from standby position Pa to discharge position Pd.

In this embodiment, while medicine receiving chamber 10 is moved from previous discharge position Pd (FIG. 1) through standby position Pa (FIG. 4) to next discharge position Pd (FIG. 1), medicine receiving chamber 10 is moved back and forth (reciprocates) from a position Pe (in which opening portions 10b of all small holes 10a of medicine receiving chamber 10 are within opening portion 5a of medicine storage chamber 5, and which is nearest to discharge position Pd), through a turn position Pa (in which opening portion 10b of all small holes 10a of medicine receiving chamber 10 are within opening portion 5a of medicine storage chamber 5, and which is furthest from the discharge position Pd), to the position Pe. During the back-and-forth (reciprocating) movement, medicine receiving chamber 10 is arranged to be moved in a state in which all opening portions 10b of medicine receiving chamber 10 are within (covered by) opening portion 5a of medicine storage chamber 5. Accordingly, a radial width W1 of opening portion 5a of medicine storage chamber 5 is longer than a radial width W0 of forming region of medicine receiving chamber 10, as shown in FIG. 1. An angle θ1 of medicine storage chamber 5 is greater than an angle θ0 of the forming region of medicine receiving chamber 10, as shown in FIG. 4. Besides, the positions Pc and Pe are filling positions Pb.

In this embodiment, opening portions 10b of the plurality of small holes 10a of medicine receiving chamber 10 are arranged to be moved radially outside a center of opening portions 5a (center in the plan view), as shown in FIG. 4.

As mentioned above, there is provided the one section in which medicine receiving chamber 10 is moved from the standby position Pa to the discharge position Pd in the state in which all opening portions 10b of medicine receiving chamber 10 are within (covered by) opening portion 5a of medicine storage chamber 5.

By the investigation of the inventors, it is understood that it is possible to further uniformalize (even) the density of powder medicine M by flowing powder medicine M within medicine receiving chamber 10, and thereby to improve the filling rate of powder medicine M. In this example, powder medicine M can flow within medicine receiving chamber 10 by the friction while medicine receiving chamber 10 is moved in the state in which all opening portions 10b of medicine receiving chamber 10 are connected with opening portion 5a of medicine storage chamber 5. Therefore, it is possible to increase the filling rate of powder medicine M to medicine receiving chamber 10.

In this embodiment, upper body 2 and lower body 3 are relatively pivoted about pivot axis Ax, and each of small holes 10a of medicine receiving chamber 10 has a semiround (hemispherical) shape. Accordingly, in the state in which opening portions 10b of medicine receiving chamber 10 is connected with opening portion 5a of medicine storage chamber 5, it is possible to smoothly flow powder medicine M along inner walls of small holes 10a of medicine receiving chamber 10, and thereby to improve the filling rate. The shape of each small hole 10a is not limited to the semiround shape, and it is optional to employ, as the shape of each small holes 10 of medicine receiving chamber 10, a bottomed cylindrical shape and so on which has a substantially curved continuous inner wall. Thereby, it is possible to obtain the same effect as the shape of the semiround shape.

In this example, there is provided the one section (Pe→Pc→Pe) in which medicine receiving chamber 10 is moved back and forth in the state in which all opening portions 10b of medicine receiving chamber 10 are within opening portion 5 of medicine storage chamber 5.

Accordingly, it is possible to invert the flow directions of powder medicine M within medicine receiving chamber 10 in the passage (Pe→Pc) and in the return passage (Pc→Pe). It is possible to suppress the bias of the density of powder medicine M within medicine receiving chamber 10, relative to case in which powder medicine M flows only in one direction during the relative pivot movement, and to further improve the filling rate.

In this embodiment, upper body 2 and lower body 3 are relatively pivoted about pivot axis Ax extending in the substantially upward and downward directions. Some of opening portions 10b are arranged to be moved radially outside the center C of opening portion 5a of medicine storage chamber 5.

The relative flow velocity of powder medicine M within medicine receiving chamber 10 increases as medicine receiving chamber 10 is moved radially outside pivot shaft Ax with respect to center C of opening portion 5a. Accordingly, it is possible to largely (widely) flow powder medicine M within medicine receiving chamber 10. Moreover, it is possible to suppress the bias of the density of powder medicine M within medicine receiving chamber 10, and to further improve the efficiency of the filling.

In this embodiment, medicine storage chamber 5 includes inclined surfaces 5b which are located at the edges of opening portion 5a in the relative sliding direction, and which are inclined so that the opening area of opening portion 5a increases toward the open side.

Inclined surfaces 5b function to fill powder medicine M to medicine receiving chamber 10 when medicine receiving chamber 10 is relatively slid below opening portion 5a. Accordingly, it is possible to improve the efficiency of the filling of powder medicine M to medicine receiving chamber 10.

In this embodiment, there are provided the plurality of small holes 10a of medicine receiving chamber 10 which are concurrently connected with opening portion 5a of medicine storage chamber 5, and which are concurrently connected with air passage 6 in the discharge position Pd.

In a case in which medicine receiving chamber 10 is provided as one large hole, variation of the filling rate of powder medicine M tends to generate by the influence of the movement of powder medicine M in the other area within medicine receiving chamber 10. On the other hand, in this embodiment, medicine receiving chamber 10 is segmented to the plurality of the small holes 10a. The plurality of the small holes 10a serve as one medicine receiving chamber 10, and accordingly it is possible to suppress the influence of the other area, and to improve the rate of the filling of the powder medicine.

In this embodiment, all of the lower opening portions 10b of the medicine receiving chambers 10a are arranged to be within the upper opening portion 5a of the medicine storage chamber 5 in the one section.

In a case in which the plurality of small holes 10a are separately connected with opening portion 5a, the variation of the pressure is generated by own weight of powder medicine M when powder medicine M is filled into each small holes 10a, and accordingly the variation of the filling rate may be generated. On the other hand, in this embodiment, all of the lower opening portions 10b of the medicine receiving chambers 10a are arranged to be within the upper opening portion 5a of the medicine storage chamber 5 in the one section. Accordingly, it is possible to uniformalize the filling pressure of powder medicine M to each small hole 10a, to decrease the filling variation, and to improve the filling rate.

Second Embodiment

Figure 10:
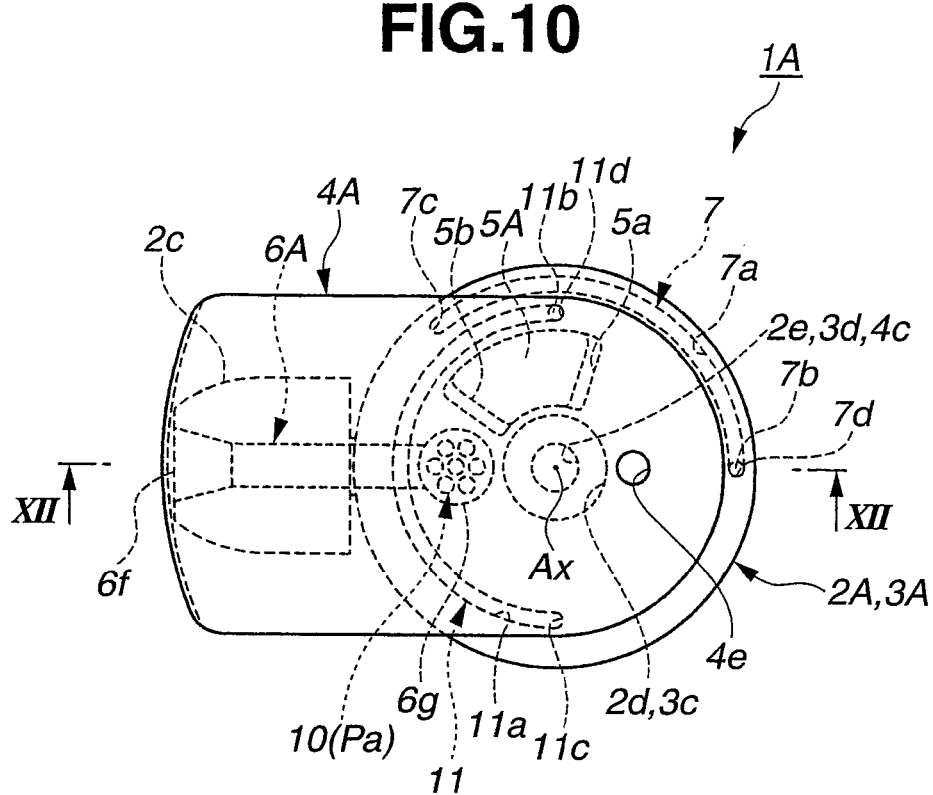
FIG. 10 is a plan view (top view) showing a powder medicine administering apparatus in a non-use state, according to a second embodiment of the present invention.
Figure 11:
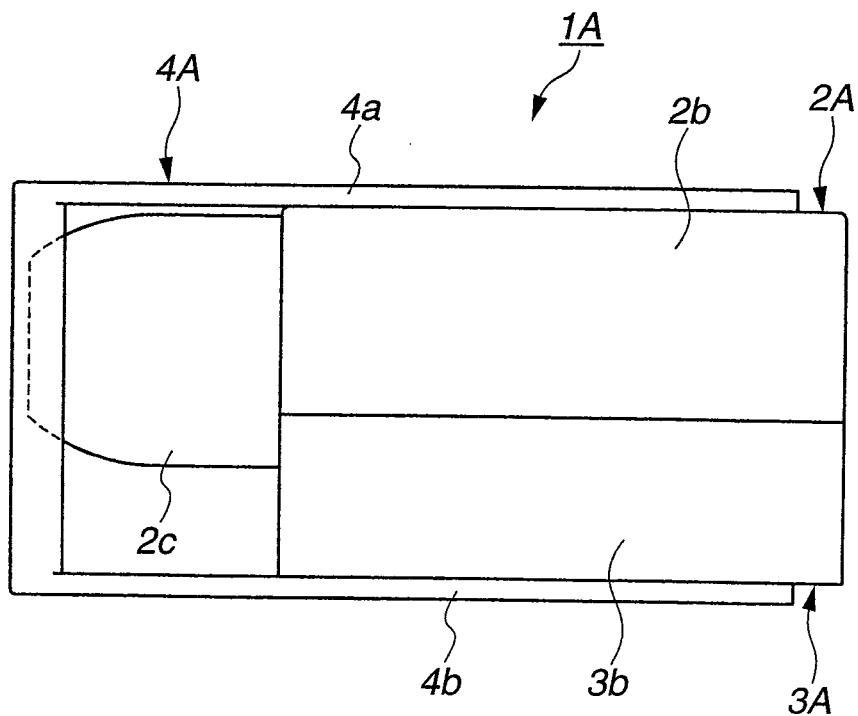
FIG. 11 is a side view showing the powder medicine administering apparatus of FIG. 10 in the non-use state.
Figure 12:
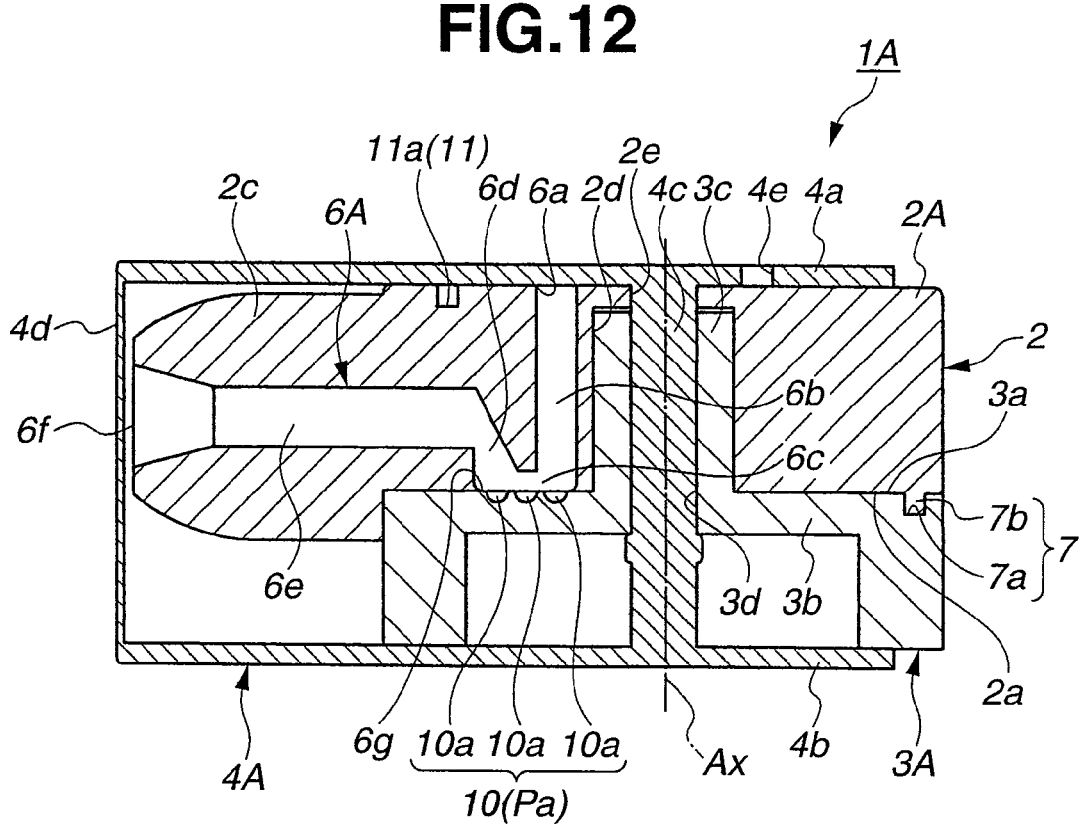
FIG. 12 is a sectional view taken along a section line XII-XII of FIG. 10.
Figure 13:
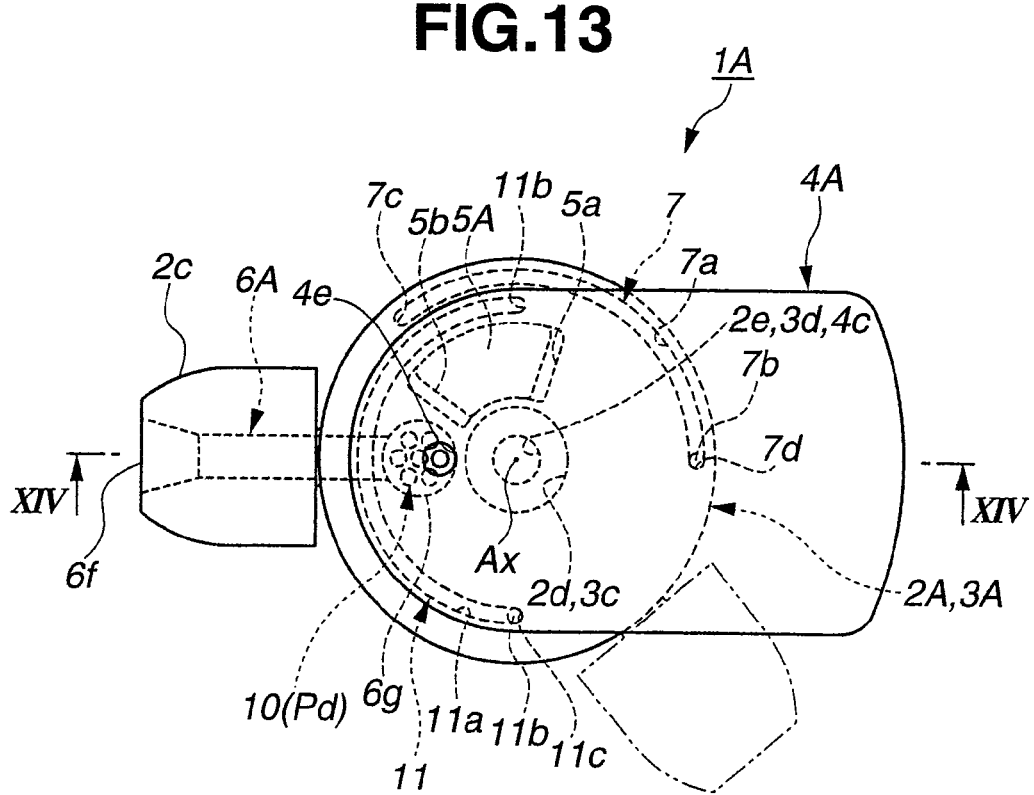
FIG. 13 is a plan view (top view) showing the powder medicine administering apparatus of FIG. 10 in a use state.
Figure 14:
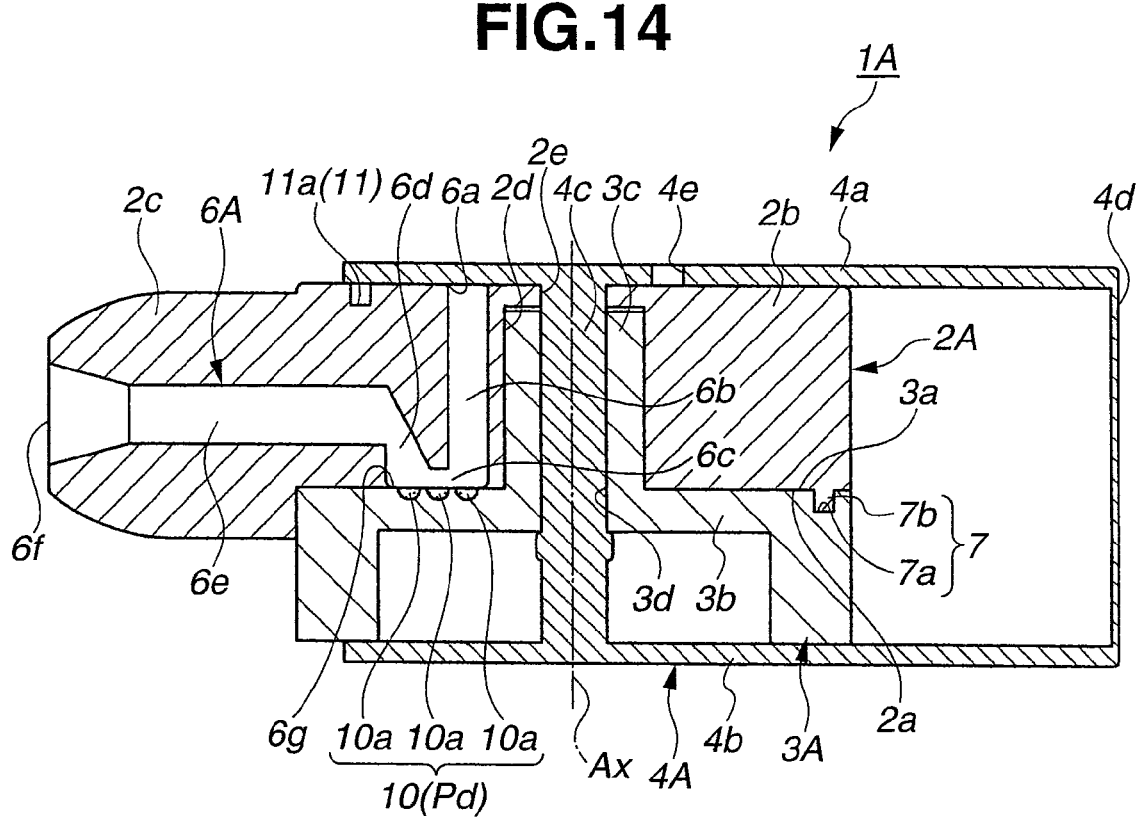
FIG. 14 is a sectional view taken along a section line XIV-XIV of FIG. 13.

FIGS. 10-21 show a powder medicine administering apparatus according to a second embodiment of the present invention. FIG. 10 is a plan (top) view showing the powder medicine administering apparatus in the non-use state. FIG. 11 is a side view showing the powder medicine administering apparatus in the non-use state. FIG. 12 is a sectional view taken along a section line of XII-XII of FIG. 10. FIG. 13 is a plan (top) view showing the powder medicine administering apparatus in the use state. FIG. 14 is a sectional view taken along a section line XIV-XIV of FIG. 13. In this embodiment, the invention is applied to the powder medicine administering apparatus of the oral type.

As shown in FIGS. 11 and 12, powder medicine administering apparatus 1A includes an upper body 2A and a lower body 3A which are arranged to be relatively slid with each other. Upper body 2 and lower body 3 includes, respectively, disc portions 2b and 3b which are overlapped with each other in substantially entire areas in the upward and downward directions. Disc portion 2b of upper body 2A includes a substantially annular lower surface 2a. Disc portion 3b of lower body 3A includes a substantially annular upper surface 3a arranged to be slid on lower surface 2a of disc portion 2b. Upper body 2A includes a substantially cylindrical bearing portion 2d which is located at a substantially central portion of disc portion 2b, which is opened in lower surface 2a, and which vertically extends from lower surface 2a in the upward direction. Disc portion 3b includes a substantially cylindrical shaft portion 3c which is located at a substantially central portion of disc portion 3b, and which vertically extends from upper surface 3a in the upward direction. Shaft portion 3c of disc portion 3b is pivotally inserted into bearing portion 2d of disc portion 2b. Accordingly, upper body 2A and lower body 3A are relatively pivoted (slid) about pivot axis Ax which is a central axis of bearing portion 2d and shaft portion 3c. Therefore, lower surface 2a of disc portion 2b and upper surface 3a of disc portion 3b are slid in the circumferential direction.

As shown in FIGS. 10~14, upper body 2A includes a tubular (cylindrical) portion 2c which is located on a side surface of disc portion 2b of upper body 2A, and which extends radially outwards. As shown in FIGS. 10 and 12, tubular portion 2c includes an air passage 6A having a discharge opening 6f located at an end portion of tubular portion 2c. The air and the powder medicine (stirred flow of the air and the powder medicine) are discharged from discharge opening 6f of air passage 6A.

As shown in FIGS. 10-14, in this embodiment, there is provided a slide cover 4A arranged to cover discharge opening 6f. This slide cover 4A includes substantially rectangular plate portions 4a and 4b sandwiching disc portions 2b and 3b from the outside in the upward and downward directions; a substantially cylindrical shaft portion 4c which is inserted through a through hole 2e of disc portion 2b and a through hole 3d of cylindrical shaft portion 3c, and which extends between plates 4a and 4b; and a plate-shaped cover portion 4d which extends between end portions of plate portions 4a and 4b, and which is curved into an arc shape covering the end portion of tubular portion 2c in the non-use state as shown in FIGS. 10-12. Shaft portion 4c is pivotally supported by through hole 3d (2e) which serves as a bearing. Consequently, slide cover 4A, upper body 2A and lower body 3A are relatively pivoted about the central axis of shaft portion 4c and through hole 3d (2e).

As shown in FIG. 12, slide cover 4A includes a through hole 4e formed in upper plate portion 4a of slide cover 4A. In the non-use state shown in FIGS. 10-12, upper plate portion 4a of slide cover 4A covers inlet opening 6a of air passage 6A, and cover portion 4d of slide cover 4A covers discharge opening 6f of air passage 6. On the other hand, in the use state shown in FIGS. 13 and 14, upper body 2A and slide cover 4A are relatively pivoted (slid), cover portion 4d of slide cover 4A opens discharge opening 6f of air passage 6A, and through hole 4e of slide cover 4A is overlapped with inlet opening 6a of air passage 6A. Accordingly, the inlet side and the outlet side of air passage 6A are connected with the outside air, and it is possible to flow the air in air passage 6A.

Air passage 6A is formed in upper body 2A, as shown in FIGS. 12 and 14. Air passage 6A includes an inlet opening 6a opened in an upper surface of upper body 2A; a passage 6b penetrating from inlet opening 6a within upper body 2A in the upward and downward directions; a passage 6c which is formed by closing an opening portion 6g opened in lower surface 2a by upper surface 3a of lower body 3A, and which serves as a return point at the lower end; a passage 6d extending from passage 6c in the upward direction; and a passage 6e extending laterally from the upper end of passage 6d through the middle portion of tubular portion 2c to discharge opening 6f.

As shown in FIGS. 13 and 14, in the use state, opening portion 6g is overlapped with powder medicine receiving chamber 10 filled with powder medicine M, and powder medicine receiving chamber 10 is connected with (confronts) air passage 6A. In this use state, medicine receiving chamber 10 is located in discharge position Pd. In this use state, the user holds tubular portion 2c in the user's mouth, and sucks. Consequently, the air flow is generated in air passage 6A, the air and powder medicine M within medicine receiving chamber 10 are stirred in passages 6c. The mixed flow of the air and powder medicine M is absorbed from discharge opening 6f to the user's mouth.

As shown in FIGS. 10 and 12-14, in this embodiment, there is provided a guide section 7 arranged to guide upper body 2A and lower body 3A for the relative sliding movement, and to define movable range of the relative pivot movement. Guide section 7 includes an arc groove 7a formed in upper surface 3a of lower body 3A along the circumferential direction of the relative pivot movement; and a protrusion 7b formed on a lower surface 2a of upper body 2A, and arranged to be inserted into groove 7a, and to move within groove 7a in connection with the relative pivot movement. Protrusion 7b is arranged to abut on longitudinal ends 7c and 7d of groove 7a to limit the range of the relative pivot movement of upper body 2A and lower body 3A. That is, this guide section 7 serves as a retaining section (stopper) to retain upper body 2A and lower body 3d.

In this embodiment, there is provided a guide section 11 arranged to guide upper body 2A and slide cover 4A for the relative sliding movement, and to limit the range of the relative movement of upper body 2A and slide cover 4A. Guide section 11 includes arc groove 11a formed in the upper surface of upper body 2A along the circumferential direction of the relative pivot movement; and a protrusion 11b formed on the lower surface of upper plate portion 4a of slide cover 4A, and arranged to be inserted into groove 11a, and to move within groove 11a in connection with the relative pivot movement. Protrusion 11b abuts on longitudinal ends 11c and 11d of groove 11a to limit the range of the relative pivot movement of the upper body 2A and slide cover 4A.

Figure 15:
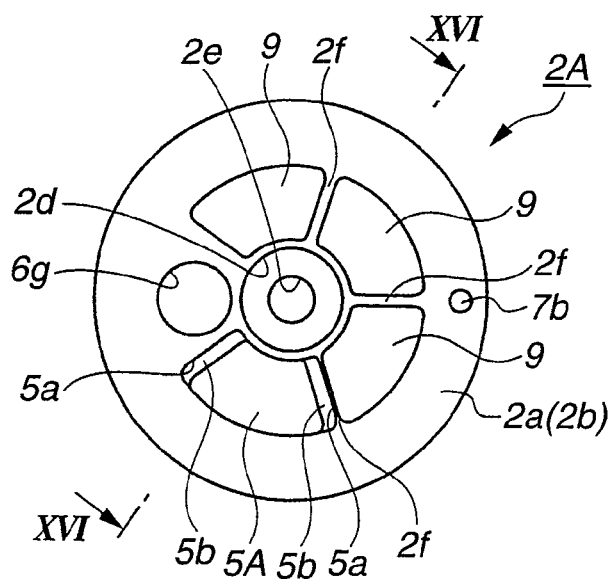
FIG. 15 is a bottom view showing an upper body of the powder medicine administering apparatus of FIG. 10.
Figure 16:
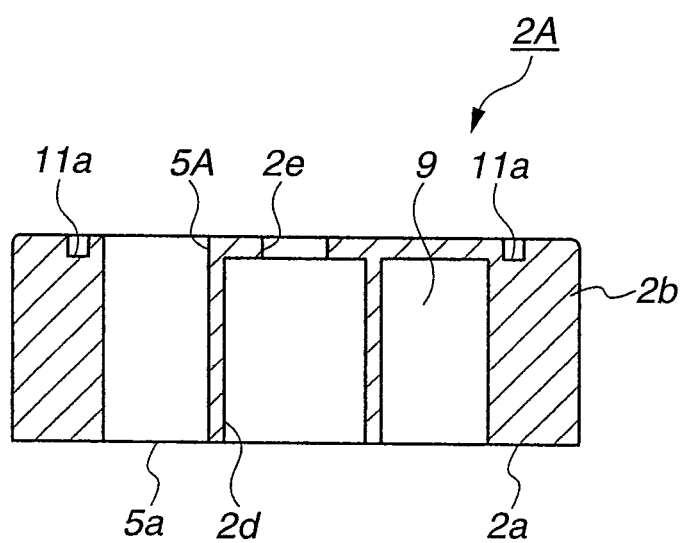
FIG. 16 is a sectional view taken along a section line XVI-XVI of FIG. 15.

FIGS. 15 and 16 show the upper body. FIG. 15 is a bottom view showing the upper body. FIG. 16 is a sectional view taken along a section line XVI-XVI of FIG. 15. Medicine storage chamber 5A storing powder medicine M is a substantially sealed space surrounded by a through hole penetrating through disk portion 2b of upper body 2A in the upward and downward directions, and having a substantially sectorial section which is concentric with bearing portion 2d and through hole 2e, upper surface 3a of lower body 3A which closes the lower end of the through hole, and a cap which closes the upper end of the through hole. An end portion of the through hole is an opening portion (upper opening portion) 5a. Powder medicine M within medicine storage chamber 5A is filled through this opening portion 5a to medicine receiving chamber 10 formed in upper surface 3a of lower body 3A. The filling of powder medicine M to medicine receiving chamber 10 will be illustrated later.

Like the first embodiment, opening portion 5a includes inclined surfaces 5b which are located at both circumferential ends of opening portion 5a in the circumferential direction (relative sliding direction), whose edges are cut off (chamfered), and which are inclined so that the opening area of opening portion 5a increases toward the open side (the upper surface 3a's side). Medicine receiving chamber 10 has a structure identical to the structure according to the first embodiment.

As shown in FIGS. 15 and 16, disc portion 2b of upper body 2A includes a plurality of medicine recovery chambers 9 each of which has a substantially sectorial section identical to medicine storage chamber 5A, each of which is opened in the downward direction, and which are formed along the circumferential direction by a substantially same pitch. These medicine recovery chambers 9 have the same shape. Adjacent two of the medicine recovery chambers 9 are partitioned by a partition wall 2f having a predetermined thickness. A bottom surface of partition wall 2f is flush with lower surface 2a of upper body 2A, and slidably abutted on upper surface 3a of lower body 3A. This medicine recovering chambers 9 are arranged to recover powder medicine M adhered between lower surface 2a and upper surface 3a.

As shown in FIG. 15, medicine storage chamber 5A and medicine recovery chambers 9 of upper body 2A are substantially symmetrical to each other in the upward and downward directions. Accordingly, it is possible to improve the weight balance of upper body 2A, and to uniformalize the flexibility and the rigidity with respect to the sandwiching force by plate portions 4a and 4b of slide cover 4A. It is possible to prevent the variation of clearance of the sliding portions between lower surface 2a of upper body 2A and upper surface 3a of lower body 3A, and to suppress the sealing characteristic from deteriorating. Moreover, it is possible to decrease the weight of powder medicine administering apparatus 1A.

Figure 17:
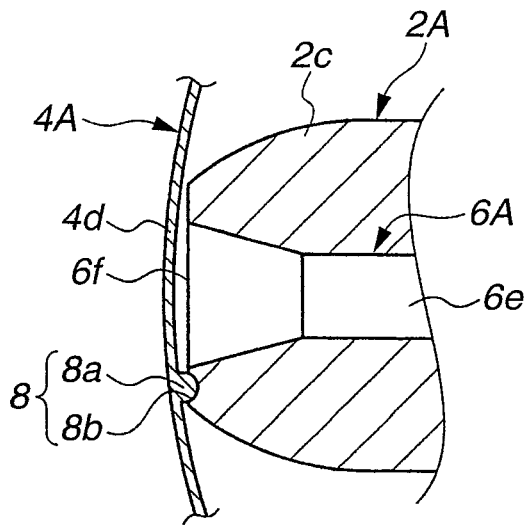
FIG. 17 is a horizontal sectional view showing an engagement section between an upper body and a slide cover of the powder medicine administering apparatus of FIG. 10.

FIG. 17 is a horizontal sectional view showing an engagement structure between the upper body and the slide cover. As shown in FIG. 17, there is provided an engagement section 8 in which an end portion of tubular portion 2c of upper body 2A is engaged with cover portion 4d of slide cover 4A. Engagement section 8 includes a recessed portion 8b formed in tubular portion 2c; and a protrusion 8a formed on cover portion 4d, and inserted into and engaged with recessed portion 8b. By the engagement of engagement section 8, it is possible to move upper body 2A with (in synchronism with) slide cover 4A at the relative slide movement of upper body 2A and lower body 3A. That is, it is possible to relatively pivot upper body 2A with (in synchronism with) slide cover 4A by relatively sliding slide cover 4A with respect to lower body 3A. This engagement of engagement section 8 is released by applying, between slide cover 4A and lower body 3A, a force in the circumferential direction which is equal to or greater than a predetermined magnitude.

Figure 18:
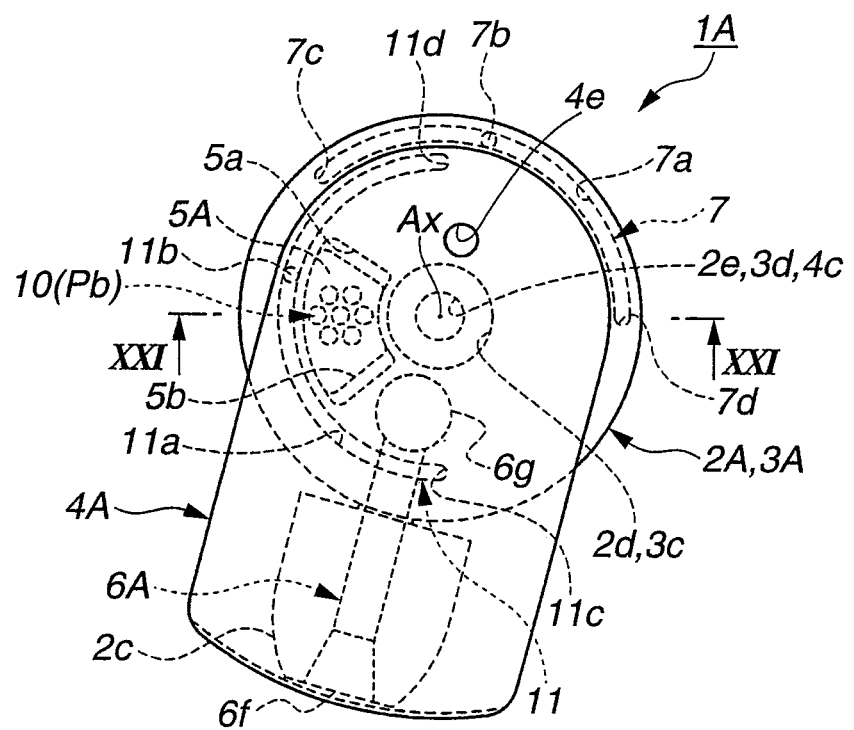
FIG. 18 is a plan view showing the powder medicine administering apparatus of FIG. 10 when the upper body and the lower body are relatively slid in one state.
Figure 19:
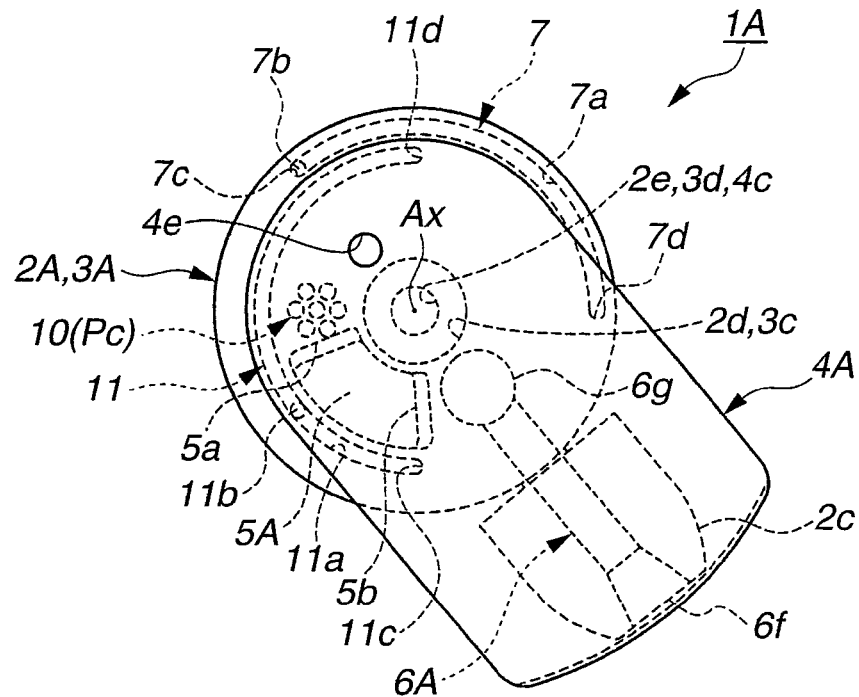
FIG. 19 is a plan view showing the powder medicine administering apparatus of FIG. 10 when the upper body and the lower body are relatively slid in another state.
Figure 20:
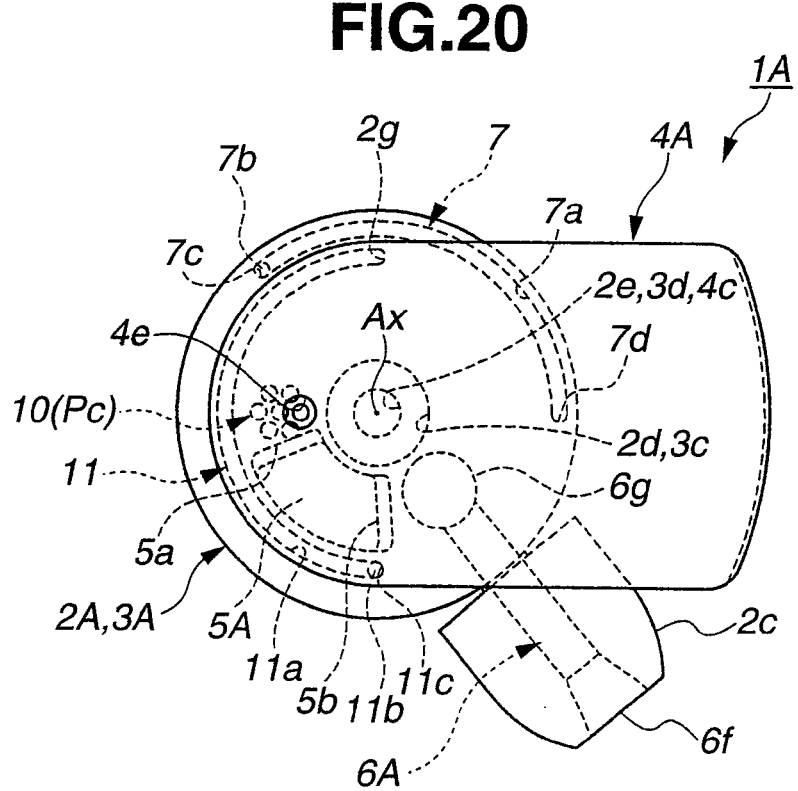
FIG. 20 is a plan view showing the powder medicine administering apparatus of FIG. 10 when the upper body and the lower body are relatively slid in still another state.
Figure 21:
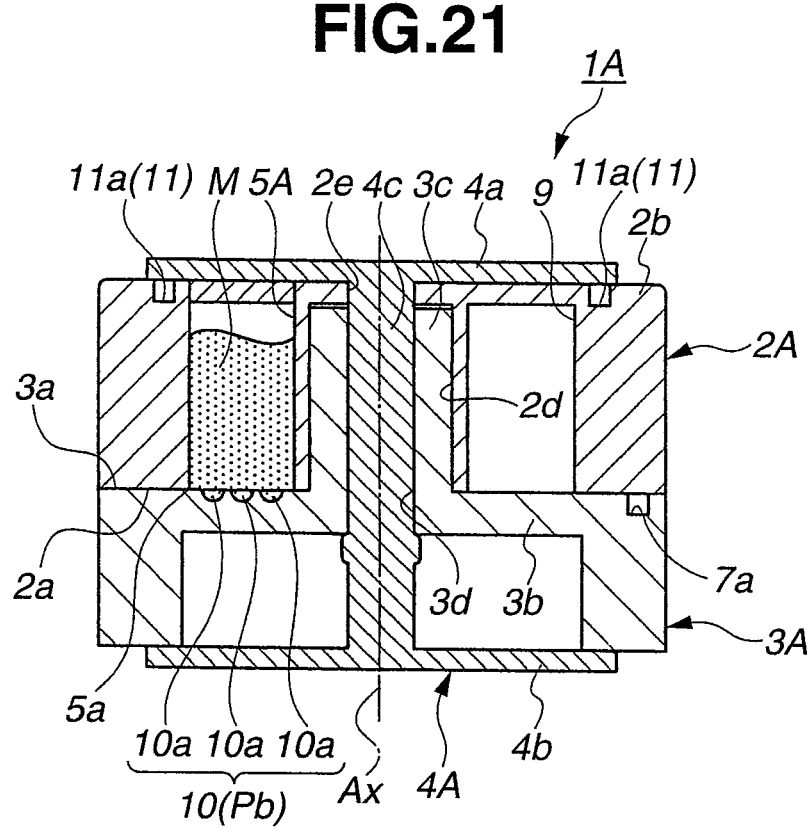
FIG. 21 is a sectional view taken along a section line XXI-XXI of FIG. 18.

FIGS. 18-20 show a plan view showing steps that the upper body and the lower body are relatively slid. FIG. 21 is a sectional view taken along a section line XXI-XXI of FIG. 18.

FIGS. 10 and 12 show the non-use state (the still standing state). In this case, medicine receiving chamber 10 is positioned in the standby position Pa. In the standby position Pa, medicine receiving chamber 10 is connected through opening portion 6g to the substantially sealed air passage 6A. Opening portion 5a of medicine storage chamber 5A and medicine receiving chamber 10 are in the non connection state.

When slide cover 4A is relatively pivoted with respect to lower body 3A from the state of FIGS. 10 and 12 in the counterclockwise direction of FIG. 10, upper body 2A engaged with slide cover 4A by engagement section 8 is moved as a unit with slide cover 4A to be brought to the state shown in FIGS. 18 and 21.

In the state shown in FIGS. 18 and 21, opening portion 5a of medicine storage chamber 5A is overlapped with medicine receiving chamber 10. As shown in FIG. 21, powder medicine M within medicine storage chamber 5A is filled through opening portion 5a of medicine storage chamber 5 in medicine receiving chamber 10. In this state, medicine receiving chamber 10 is in the filling position Pb, and opening portion 5a of medicine storage chamber 5A and medicine receiving chamber 10 are in the connection state. As shown in FIG. 18, all of the plurality of small holes 10a of medicine receiving chamber 10 are within (covered by) opening portion 5a of medicine storage chamber 5A.

Moreover, slide cover 4A is relatively slid with respect to lower body 3A in the counterclockwise direction of FIG. 18 to be brought to the state shown in FIG. 19. In the guide section 7 of upper body 2A and lower body 3A, protrusion 7b of guide section 7 is abutted on and retained by longitudinal end 7c of groove 7a, so that upper body 2A can not be further pivoted with respect to lower body 3A from the state of FIG. 19 in the counterclockwise direction. On the other hand, in the guide section 11 of upper body 2A and slide cover 4A, protrusion 11b is on the way of groove 11a, and not abutted on longitudinal end 11c. Accordingly, slide cover 4A can be further pivoted from the state of FIG. 19 in the counterclockwise direction. Therefore, when slide cover 4A is pivoted with respect to lower body 3A in the counterclockwise direction by applying the force which is equal to or greater than the predetermined magnitude in the state of FIG. 19, the engagement of upper body 2A and slide cover 4A by engagement section 8 is released, and the only slide cover 4A is pivoted in the counterclockwise direction to be brought to the state of FIG. 20. When slide cover 4A is pivoted from the state of FIG. 19 to the state of FIG. 20, cover portion 4d (cf. FIG. 12) of slide cover 4A opens discharge opening 6f at the end portion of tubular portion 2c of upper body 2A.

As mentioned above, the powder medicine administering apparatus is brought from the state of FIG. 10 through the state of FIG. 18 to the state of FIG. 19. Consequently, the position relationship between opening portion 5a of medicine storage chamber 5A and medicine receiving chamber 10 is varied, and opening portion 5a passes above medicine receiving chamber 10 in the relative slide direction (in the circumferential direction, in the counterclockwise direction of FIGS. 10, 13, and 18-20). That is, medicine receiving chamber 10 passes below opening portion 5a in the relative slide direction (in the circumferential direction, in the clockwise direction of FIGS. 10, 13, and 18-20). While medicine receiving chamber 10 is overlapped with opening portion 5a, powder medicine M is filled through opening portion 5a to medicine receiving chamber 10. After the medicine receiving chamber 10 is not overlapped with opening portion 5a, powder medicine M of medicine receiving chamber 10 is leveled by lower surface 2a of upper body 2A. That is, the above transition from the state of FIG. 10 through the state of FIG. 18 to the state FIG. 19 is one stroke that opening portion 5a and medicine receiving chamber 10 are brought from the non-connection state through the connection state to introduce powder medicine M into medicine receiving chamber 10, and to level powder medicine M.

Moreover, the only upper body 2A separated from slide cover 4A in FIG. 20 is relatively slid in a direction opposite to the transition of FIGS. 10, 18 and 19 to be brought to the state of FIG. 13. In the transition from the state of FIG. 20 to the state of FIG. 13, the position relationship between opening portion 5a of medicine storage chamber 5A and medicine receiving chamber 10 is varied, opening portion 5a passes above medicine receiving chamber 10 in the relative slide direction (in the circumferential direction, in the clockwise direction of FIGS. 10, 13 and 18~20). That is, medicine receiving chamber 10 passes below opening portion 5a in the relative slide direction (in the circumferential direction, in the counterclockwise direction of FIGS. 10, 13 and 18~20). That is, the transition from the state of FIG. 20 to the state of FIG. 13 is further one stroke in which opening portion 5a and medicine receiving chamber 10 are from the non-connection state through the connection state to the non-connection state to supply powder medicine M to medicine receiving chamber 10, and to level powder medicine M. In the state of FIGS. 19 and 20, medicine receiving chamber 10 is in the return position Pc, and opening portion 5a of medicine storage chamber 5A and medicine receiving chamber 10 are in the non-connection state. The transition from the state of FIG. 19 to the state of FIG. 20 (slide cover 4A is separated from upper body portion 2A and pivoted independently) is performed after medicine receiving chamber 10 passes below opening portion 5a completely.

In this embodiment, medicine receiving chamber 10 passes below opening portion 5a in the relative slide direction more than one (that is, two strokes in the opposite directions). That is, medicine receiving chamber 10 moves back and forth once across opening portion 5a in the relative slide direction. Subsequently, medicine receiving chamber 10 reaches the discharge position Pd so that the powder medicine administering apparatus becomes the use (usable) state shown in FIGS. 13 and 14. In this state, medicine receiving chamber 10 filled with powder medicine M is connected with air passage 6A. Inlet opening 6a and outlet opening 6f of air passage 6A are connected with the outside air, and the air can flow through air passage 6A. When the air flow is generated in air passage 6A by the suction of the user and the air entered from passage 6b flows through passages 6c and 6d, the flow separation and the turbulent are generated since passage 6c confronting medicine receiving chamber 10 is the return point. Therefore, it is possible to effectively raise up and stir powder medicine M filled in medicine receiving chamber 10, and to suppress the powder medicine M from remaining in powder medicine administering apparatus 1A. It is possible to improve the efficiency of the administration of powder medicine M.

In this embodiment, there is provided a one section in which medicine receiving chamber 10 is moved in the state in which all opening portions 10b of medicine receiving chamber 10 is within opening portion 5a of medicine storage chamber 5 while medicine receiving chamber 10 is moved from standby position Pa to discharge position Pd.

In this example, powder medicine M flows within medicine receiving chamber 10 by the friction while medicine receiving chamber 10 is moved in the state in which all opening portions 10b of medicine receiving chamber 10 are connected with opening portion 5a of medicine storage chamber 5. Therefore, it is possible to the filling rate of powder medicine M to medicine receiving chamber 10.

In this embodiment, the medicine receiving chamber 10 reaches the discharge position Pd after at least two strokes that the medicine receiving chamber 10 is switched from the non-connection state through the connection state to the non-connection state by passing the medicine receiving chamber 10 below the upper opening portion 5a of the medicine storage chamber 5 by the relative slide movement of the upper body 2 and the lower body 3 to supply and level the powder medicine M.

In this way, a plurality of stroke of the supply of powder medicine M to medicine receiving chamber 10 and the leveling of the powder medicine M are performed, and accordingly the number of the filling of powder medicine M to medicine receiving chamber 10 is increased. Therefore, it is possible to further uniformalize the clearances among the particles, and to improve the filling rate.

In this example, medicine receiving chamber 10 reaches the discharge position Pd after the multiple strokes that the relative slide movements are in different directions (two strokes in the opposite directions in this example).

The density of the powder medicine M within medicine receiving chamber 10 in the filled state may be dependent on the movement direction of the medicine receiving chamber 10. Accordingly, in this embodiment, medicine receiving chamber 10 reaches discharge position Pd after the multiple strokes in the different relative slide directions, and it is possible to decrease the variation of the filled state of medicine receiving chamber 10. In this embodiment, medicine receiving chamber 10 reaches discharge position Pd after the two strokes in the opposite directions. However, it is optional to employ two or more strokes, and to employ different directions such as the crossing directions other than the opposite directions.

As mentioned above, medicine receiving chamber 10 reaches discharge position Pd after two strokes of the different relative slide directions.

By the leveling, the filling rate of the powder medicine becomes low in an end portion of medicine receiving chamber 10 on the forward side of the movement direction with respect to opening portion 5a. In this embodiment, medicine receiving chamber 10 reaches discharge position Pd after the two strokes in the different relative slide directions. The two strokes are in the opposite directions of the forward and rearward directions, and accordingly it is possible to decrease the variation of the filled state of medicine receiving chamber 10.

In this embodiment, by the relative slide movement of upper body 2A and lower body 3A, medicine receiving chamber 10 moves back and forth (reciprocates) across opening portion 5a.

That is, medicine receiving chamber 10 moves back and forth in path across opening portion 5a, and it is possible to readily gain a structure in which medicine receiving chamber 10 reaches discharge position Pd after the two strokes in the different relative slide directions. Moreover, it is possible to set the discharge position Pd and the standby position Pa in the non-use state on the same side of the relative slide direction with respect to opening portion 5a. Accordingly, the user can surely recognize, as ready movement before the administration, the back-and-forth relative slide movement of upper body 2A and lower body 3A from the state in which medicine receiving chamber 10 is in the standby position Pa.

In this embodiment, slide cover 4 is arranged to be slid with one of upper body 2A and lower body 3A (upper body 2A in this embodiment), and to open and close discharge opening 6 for powder medicine M and the air. When this slide cover 4A is slid from the close position to close discharge opening 6f to the open position to open discharge opening 6f, the one of upper body 2A and lower body 3A (upper body 2A in this embodiment) is relatively is slid with respect to the other of upper body 2A and lower body 3A (lower body 3A in this embodiment).

Accordingly, it is possible to omit the trouble of the ready operation before the administration, relative to the case in which the relative slide operation of upper body 2A and lower body 3A and the operation of opening slide cover 4A are independently set. The operation of opening discharge opening 6f by slide cover 4A is readily recognized as the ready operation before the administration. Accordingly, upper body 2A and lower body 3A are relatively slid by the above-described operation, and it is possible to surely perform the relative slide operation.

In this embodiment, the medicine receiving chamber 10 reaches the discharge position Pd after the two strokes which are in the opposite directions; and the medicine receiving chamber 10 is moved in a first stroke when the slide cover 4A is slid to the open position to open discharge opening 6f; and the medicine receiving chamber 10 is moved in a second stroke which is in a direction opposite to the first stroke when the one of the upper body 2A and the lower body 3A is returned to the standby position Pa before the one of the upper body 2A and the lower body 3A is moved with the slide cover 4A after the slide cover 4A is separated from the one of the upper body 2A and the lower body 3A (upper body 2A in this embodiment).

That is, the operation of opening slide cover 4A generates the relative slide movement of upper body 2A and lower body 3A, the connection state between slide cover 4A and upper body 2A is dissolved. Then, slide cover 4a is held in the open state, the only one of upper body 2A and lower body 3A (upper body 2A in this embodiment) which moves in synchronism with the above movement is returned to the original position. By the above-described simple operation, upper body 2A and lower body 3A are relatively slid in the opposite directions, and it is possible to improve the filling rate of powder medicine M to medicine receiving chamber 10.

In this embodiment, engagement section 8 engages slide cover 4A and the one of upper body 2A and lower body 3A (upper body 2A in this embodiment) to move slide cover 4a with the one of upper body 2A and lower body 3A. Guide section 7 serves as the retaining section arranged to retain the one of upper body 2A and lower body 3A (upper body 2A in this embodiment) which moves with slide cover 4A, to the other of upper body 2A and lower body 3A (lower body 3A in this embodiment), after medicine receiving chamber 10 passes below opening portion 5a by the relative slide movement in synchronism with the operation of opening discharge opening 6f of slide cover 4A. By the above operation, the engagement of slide cover 4A and the one of upper body 2A and lower body 3A (upper body 2A in this embodiment) is released.

Accordingly, it is possible to readily separate the slide cover 4a and the one of upper body 2A and lower body 3A (upper body 2A in this embodiment) which moves with slide cover 4A.

In this embodiment, opening portion 5a has a size larger than opening portion (lower opening portion) 10b of medicine receiving chamber 10. Accordingly, opening portion 10b can be within opening portion 5a in the connection state of opening portion 5a and medicine receiving chamber 10.

Therefore, it is possible to increase the one section in which medicine receiving chamber 10 is connected with opening portion 5a of medicine storage chamber 5 at the relative slide movement, and to improve the filling rate of powder medicine M to medicine receiving chamber 10.

In this embodiment, there are provided the plurality of small holes 10a of medicine receiving chamber 10 which are concurrently communicated with opening portion 5a, and which are concurrently communicated with air passage 6A.

In a case in which medicine receiving chamber 10 is provided as one large hole, variation of the filling rate of powder medicine M tends to generate by the influence of the movement of powder medicine M in the other area within medicine receiving chamber 10. On the other hand, in this embodiment, medicine receiving chamber 10 is segmented to the plurality of the small holes 10a. The plurality of the small holes 10a serve as one medicine receiving chamber 10, and accordingly it is possible to suppress the influence of the other area, and to improve the rate of the filling of the powder medicine.

In this embodiment, all of the lower opening portions 10b of the medicine receiving chambers 10a are arranged to be within the upper opening portion 5a of the medicine storage chamber 5 in the one section.

In a case in which the plurality of small holes 10a are separately connected with opening portion 5a, the variation of the pressure is generated by own weight of powder medicine M when powder medicine M is filled into each small holes 10a, and accordingly the variation of the filling rate may be generated. On the other hand, in this embodiment, it is possible to uniformalize the filling pressure of powder medicine M to each small hole 10a, to decrease the filling variation, and to improve the filling rate.

In this embodiment, the powder medicine administering apparatus further includes a medicine recovery chamber 9 arranged to recover the powder medicine M, and located at a position which is separated from the upper opening portion 5a of medicine storage chamber 5 in the relative slide direction, or at a position which is separated from the medicine receiving chamber 10 of the lower body 3 in the relative slide direction.

In the case in which powder medicine M remains between lower surface 2a of upper body 2A and upper surface 3a of lower body 3A, the gap generates between lower surface 2a and upper surface 3a, and the sealing characteristic may be deteriorated. In this embodiment, medicine recovering chamber 9 recovers the powder medicine adhered between lower surface 2a and upper surface 3a, and it is possible to suppress the problems.

In this embodiment, upper body 2A and lower body 3A are slid from the non-use state by the one back-and-forth movement, and medicine receiving chamber 10 is moved back and forth below the upper opening portion 5a to reach the discharge position Pd.

Therefore, by the simple one back-and-forth relative slide operation, it is possible to suppress the decrease of the filling rate at the leveling and the supply of powder medicine M to medicine receiving chamber 10, and to improve the accuracy of the dose of powder medicine M.

Figure 22A:
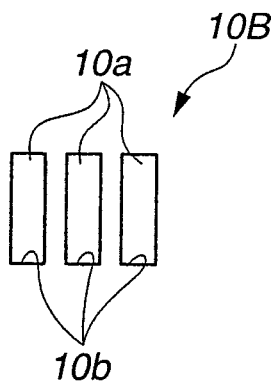
FIG. 22A is a plan view showing a medicine receiving chamber of a powder medicine administering apparatus according to a first practical example of the second embodiment of the present invention.

FIGS. 22 and 23 show practical examples of medicine receiving chambers. FIG. 22A is a plan view showing the medicine receiving chamber in a first practical example according to the second embodiment of the present invention.

Figure 22B:
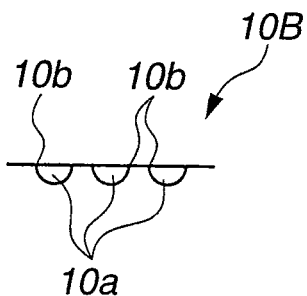
FIG. 22B is a partial sectional view showing the medicine receiving chamber of the powder medicine administering apparatus of FIG. 22A.
Figure 23A:
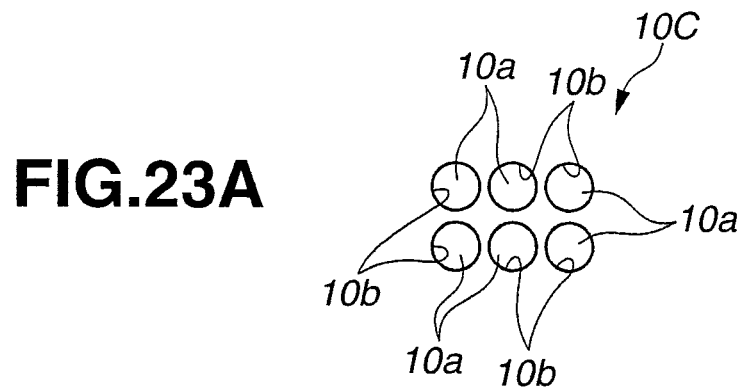
FIG. 23A is a plan view showing a medicine receiving chamber of a powder medicine administering apparatus of a second practical example of the second embodiment of the present invention.
Figure 23B:
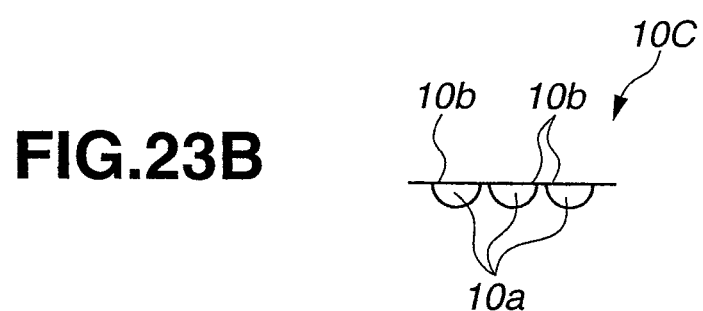
FIG. 23B is a partial sectional view showing the medicine receiving chamber of the powder medicine administering apparatus of FIG. 23A.

FIG. 22B is a partial sectional view showing the medicine receiving chamber of FIG. 22A. FIG. 23A is a plan view showing the medicine receiving chamber in a second practical example according to the second embodiment of the present invention. FIG. 23B is a partial sectional view showing the medicine receiving chamber of FIG. 23A. FIGS. 22A and 22B show a medicine receiving chamber 10B having a plurality of rectangular small holes 10a. FIGS. 23A and 23B show a medicine receiving chamber 10C in which the arrangement and the number of the plurality of small holes 10a are changed from FIG. 9. By these practical examples, it is also possible to attain the same effect. In the practical examples of FIG. 22, it is preferred to set the relative slide direction to the leftward and rightward directions of FIGS. 22A and 22B.

Figure 24:
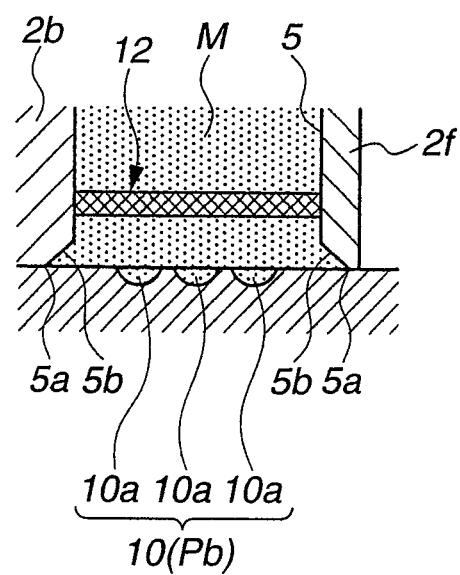
FIG. 24 is a longitudinal sectional view showing a medicine storage chamber of the powder medicine administering apparatus according to the first and second practical examples of the second embodiment of the present invention.

FIG. 24 is a longitudinal sectional view showing a practical example of medicine storage chamber 5. In this practical example, a mesh 12 is provided above opening portion 5a. By this mesh 12, it is possible to decrease the influence of the own weight of powder medicine M, and to improve the variation of the filling rate by the position of the opening portion 5a. In a case in which powder medicine M is cohered (aggregated), it is possible to keep the cohered powder medicine M on mesh 12, and to suppress the cohered powder medicine M from supplying to medicine receiving chamber 10.

Third Embodiment

FIG. 25 shows a powder medicine administering apparatus according to a third embodiment of the present invention. FIGS. 25A and 25B are views showing the powder medicine administering apparatus in which the medicine receiving chamber is on one side of the relative slide direction with respect to the medicine storage chamber. FIG. 25A is a plan view showing the powder medicine administering apparatus. FIG. 25B is a side view showing the powder medicine administering apparatus. FIG. 26 is a plan view showing the powder medicine administering apparatus in which the medicine receiving chamber is on the other side of the relative slide direction with respect to the medicine storage chamber.

In the first embodiment, upper body 2 and lower body 3 are relatively pivoted. In this third embodiment, upper body 2D and lower body 3D are relatively slid in a linear manner. Upper body 2D includes a cavity (slit) 2g having a substantially rectangular cylindrical shape elongated in a horizontal direction. Lower body 3D is in the form of a rod having a substantially rectangular section. Lower body 3D is slidably inserted into cavity 2g. Lower body 3D is pulled from the state shown in FIG. 25 in the rightward direction of FIGS. 25A and 26, and upper body 2D and lower body 3D are relatively slid. Moreover, powder medicine administering apparatus returns from the state of FIG. 26 to the state of FIG. 25. The one back-and-forth slide operation is performed.

By this linear relative slide operation, it is possible to perform the multiple back-and-forth movement of medicine receiving chamber 10 below opening portion 5a of medicine storage chamber 5D. Accordingly, it is possible to attain the same effects as the second embodiment. This embodiment is preferred when powder medicine administering apparatus 1D is formed into the elongated shape.

Fourth Embodiment

Figures 27A, 27B:
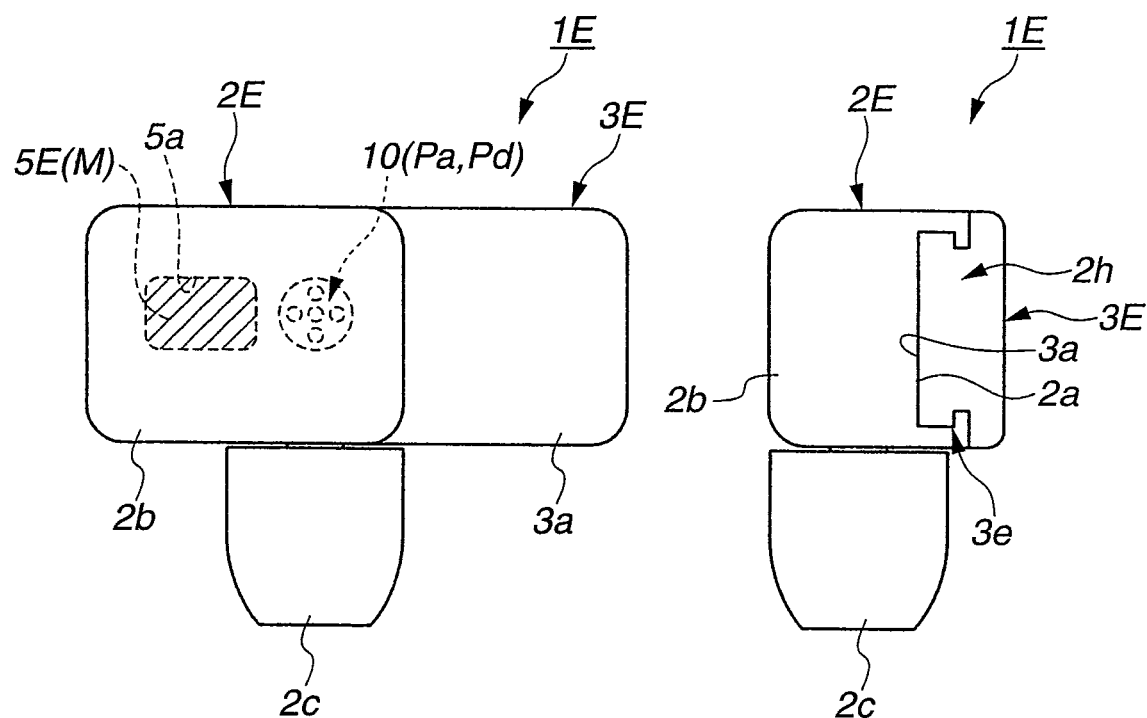
FIG. 27A is a plan view showing a powder medicine administering apparatus according to a fourth embodiment of the present invention.
FIG. 27B is a side view showing the powder medicine administering apparatus of FIG. 27A.

FIGS. 27A and 27B are views showing a powder medicine administering apparatus according to a fourth embodiment of the present invention. FIG. 27A is a plan view showing the powder medicine administering apparatus. FIG. 27B is a side view showing the powder medicine administering apparatus. The powder medicine administering apparatuses 1D of FIG. 27 is substantially identical to the powder medicine administering apparatus 1 of FIG. 1 in most aspects as shown by the use of the same reference numerals.

In the third embodiment, lower body 3D is relatively slid within cavity 2g. In this fourth embodiment, upper body 2E includes a recessed groove (dovetail way) 2h which has a substantially C-shaped section, and which is formed in a lower surface 2a of upper body 2E. Lower body 3E is arranged to be slid along recessed groove 2h of upper body 2E.

In this structure, it is also possible to perform the multiple back-and-forth movement of medicine receiving chamber 10 below opening portion 5a of medicine storage chamber 5E. Accordingly, it is also possible to attain the same effects as the first embodiment. This embodiment is also preferred when the powder medicine administering apparatus is formed into the elongated shape.

In the above described embodiment, the number of the relative slide movement is two. However, it is optional to set the number of the relative slide movement to three or more. Moreover, it is optional to perform the multiple relative slide movements in the same direction. Moreover, it is possible to vary a structure for performing the relative slide movement.

Moreover, it is optional to vary the structure of the powder medicine administering apparatus. For example, it is optional to apply the invention to a powder medicine administering apparatus which generates the air flow by compressing a volume chamber, and to apply the invention to a powder medicine administering apparatus other than the powder medicine administering apparatus for the oral use. Moreover, it is optional to vary the shape of the air passages.

Moreover, it is possible to move the slide cover with the lower body, and to form the air passage and the discharge opening in the lower body.

This application is based on a prior Japanese Patent Application No. 2007-291933 filed on Nov. 9, 2007, and a prior Japanese Patent Application No. 2008-228999 filed on Sep. 5, 2008. The entire contents of these Japanese Patent Applications No. 2007-291933 and No. 2008-228999 are hereby incorporated by reference.

Although the invention has been described above by reference to certain embodiments of the invention, the invention is not limited to the embodiments described above. Modifications and variations of the embodiments described above will occur to those skilled in the art in light of the above teachings. The scope of the invention is defined with reference to the following claims.

What is claimed is:

1. A powder medicine administering apparatus comprising:
    an upper body including a lower surface, and a medicine storage chamber having an upper opening portion opened on the lower surface, and storing a powder medicine;
    a lower body including an upper surface, and a medicine receiving chamber which has a lower opening portion, and which is recessed in a downward direction from the lower opening portion, the lower body being relatively pivoted with respect to the upper body about a pivot axis so that the lower surface of the upper body is slidably moved on the upper surface of the lower body to be switched between a connection state in which the upper opening portion of the upper body is connected with the medicine receiving chamber of the lower body, and a non-connection state in which the upper opening portion of the upper body is not connected with the medicine receiving chamber of the lower body, the medicine storage chamber of the upper body being arranged to supply the powder medicine through the upper opening portion of the upper body to the medicine receiving chamber of the lower body in the connection state, the upper body being arranged to level the powder medicine supplied to the medicine receiving chamber by the relative slide movement of the upper body and the lower body, the medicine receiving chamber being moved from a standby position to a discharge position in which the medicine receiving chamber is connected with an air passage to discharge the powder medicine with air, the medicine receiving chamber being arranged to be moved in one section from the standby position to the discharge position so that the entire lower opening portion of the medicine receiving chamber is within the upper opening portion of the upper body, wherein the medicine receiving chamber is moved back and forth in the one section from a previous discharge position through the standby position to a next discharge position so that the entire lower opening portion of the medicine receiving chamber is within the upper opening portion of the medicine storage chamber, and wherein the medicine receiving chamber reaches the next discharge position after a first stroke, in which the medicine receiving chamber is moved from the previous discharge position to a return position so as to be switched from the non-connection state through the connection state to the non-connection state by passing the medicine receiving chamber below the upper opening portion of the medicine storage chamber by the relative slide movement of the upper body and the lower body to supply and level the powder medicine, and a second stroke, in which the medicine receiving chamber is moved from the return position to the next discharge position to be switched from the non-connection state through the connection state to the non connection state by passing the medicine receiving chamber below the upper opening portion of the medicine storage chamber by the relative slide movement of the upper body and the lower body to supply and level the powder medicine, and which is in a direction opposite to the first stroke.

2. The powder medicine administering apparatus as claimed in claim 1, wherein the medicine receiving chamber reaches the discharge position after the two strokes in which the relative slide movements are in opposite directions.

3. The powder medicine administering apparatus as claimed in claim 2, wherein the medicine receiving chamber is moved back and forth across the upper opening portion of the medicine storage chamber by the relative slide movements of the upper body and the lower body.

4. The powder medicine administering apparatus as claimed in claim 1, wherein the powder medicine administering apparatus further comprises a slide cover arranged to be slid with one of either the upper body or the lower body, and to move between an open position to open a discharge opening of the powder medicine and the air, and a close position to close the discharge opening of the powder medicine and the air; and the one of either the upper body or the lower body is relatively slid with the slide cover with respect to the other of either the upper body or the lower body when the slide cover is slid from the open position to the close position.

5. The powder medicine administering apparatus as claimed in claim 4, wherein the medicine receiving chamber reaches the discharge position after the two strokes which are in the opposite directions; and the medicine receiving chamber is moved in a first stroke when the slide cover is slid to the open position; and the medicine receiving chamber is moved in a second stroke which is in a direction opposite to the first stroke when the one of either the upper body or the lower body is returned to a position before the one of either the upper body or the lower body is moved with the slide cover, after the slide cover is separated from the one of either the upper body or the lower body.

6. The powder medicine administering apparatus as claimed in claim 5, wherein the powder medicine administering apparatus further comprises an engagement section arranged to engage the slide cover and the one of either the upper body or the lower body to move the slide cover with the one of either the upper body or the lower body; and a retaining section arranged to retain the one of either the upper body or the lower body to the other of either the upper body or the lower body after the medicine receiving chamber passes below the upper opening portion of the medicine storage chamber by the movement of the slide cover to open the discharge opening; and the engagement section releases the engagement of the slide cover and the one of either the upper body or the lower body by retaining the one of either the upper body or the lower body to the other of either the upper body or the lower body by the retaining section.

7. The powder medicine administering apparatus as claimed in claim 1, wherein the upper opening portion of the medicine storage chamber includes an inclined surface which is located at an edge of the upper opening portion in the relative slide direction, and which is inclined so that an area of the upper opening portion increases toward an open side.

8. The powder medicine administering apparatus as claimed in claim 1, wherein the lower body includes a plurality of the medicine receiving chambers arranged to be concurrently connected with the upper opening portion of the medicine storage chamber, and to be concurrently connected with the air passage in the discharge position.

9. The powder medicine administering apparatus as claimed in claim 8, wherein each of the plurality of the medicine receiving chambers has a lower opening portion; and all of the lower opening portions of the medicine receiving chambers are arranged to be within the upper opening portion of the medicine storage chamber in the one section.

10. The powder medicine administering apparatus as claimed in claim 1, wherein the pivot axis extends in substantially upward and downward directions; and the lower opening portion of the medicine receiving chamber is moved radially outside a center of the upper opening portion of the medicine storage chamber.

11. The powder medicine administering apparatus as claimed in claim 1, wherein the powder medicine administering apparatus further includes a mesh located on an upper side of the upper opening portion of the medicine storage chamber.

12. The powder medicine administering apparatus as claimed in claim 1, wherein the powder medicine administering apparatus further comprises a medicine recovery chamber arranged to recover the powder medicine, and located at a position which is separated from the upper opening portion of the medicine storage chamber in the relative slide direction, or at a-position which is separated from the medicine receiving chamber of the lower body in the relative slide direction.

13. The powder medicine administering apparatus as claimed in claim 1, wherein the upper body and the lower body are relatively pivoted about a pivot and the upper opening portion of the medicine storage chamber has a circumferential length longer than a circumferential length of the lower opening portion of the medicine receiving chamber, and a radial length longer than a radial length of the lower opening portion of the medicine receiving chamber.

14. The powder medicine administering apparatus as claimed in claim 1, wherein one of the upper and lower bodies defines a shaft portion extending along the pivot axis, and the other of the upper and lower bodies includes a section through which the shaft portion projects that is pivotable with respect to the shaft portion.

15. The powder medicine administering apparatus as claimed in claim 14, wherein the section is a circumferential inner surface of a through hole in the lower body.

16. The powder medicine administering apparatus as claimed in claim 14, wherein the section is a bearing portion of a recess in the upper body.

\* \* \* \* \*